United States Patent [19]
Chang et al.

[11] Patent Number: 5,602,170
[45] Date of Patent: Feb. 11, 1997

[54] MEDICINAL THIOPHENE COMPOUNDS

[75] Inventors: Ching-Te Chang, Taipei; Kuo-Mou Chen, Hsinchu; Wann-Huang Liu, Hsinchu; Fen-Lan Lin, Hsinchu; Rong-Tsun Wu, Taipei, all of Taiwan

[73] Assignee: Industrial Technology Research Institute, Taiwan

[21] Appl. No.: 302,278

[22] Filed: Sep. 8, 1994

Related U.S. Application Data

[63] Continuation-in-part of Ser. No. 838,516, Feb. 19, 1992, abandoned.

[51] Int. Cl.⁶ .................................................. A61K 31/38
[52] U.S. Cl. .................................................. 514/444
[58] Field of Search .................................................. 514/444

[56] References Cited

PUBLICATIONS

Hudson et al, Chemosphere (1989), 19(8–9), pp. 1329–1343.
Hudson et al., BioAct. Mol. (1988), 7, pp. 315–338.
Chemical Abstracts, vol. 114: 185179d, p. 758, 1991.
Prog. Chem. Org. Nat. Prod., vol. 56, pp. 88–169, 1991.

*Primary Examiner*—Jerome D. Goldberg
*Attorney, Agent, or Firm*—Fish & Richardson P.C.

[57] ABSTRACT

A method of treating inflammation including administering to a subject an effective amount of a compound of the following formula:

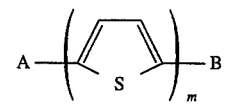

wherein m is 1–4; and each of A and B, independently, is H, $C_{1-7}$ alkyl, $C_{2-7}$ alkenyl, $C_{2-7}$ alkynyl, $(CH_2)_n CHO$, $(CH_2)_o COOH$, $C_{1-7}$ alkoxy, $C_{2-7}$ alkoxyalkyl, $C_{1-7}$ hydroxyalkyl, CN, $NO_2$, halogen, $CH(OR^1)_2$, $CO.R^1$, $NR^2R^3$ or its acid salt, $CO.NR^2R^3$, $CHR^1NR^2R^3$ or its acid salt, $CH=NR^2$, $C\equiv CR^4$, $CR^1=CR^5R^6$, $CO.CH=CHR^7$, $CH=CHR^8$, or $COOR^9$; in which each of n and o, independently, is 0–4; $R^1$ is $C_{1-4}$ alkyl or $C_{1-4}$ acyl; each of $R^2$ and $R^3$, independently is H, $C_{1-4}$ alkyl, or $C_{1-4}$ hydroxyalkyl; $R^4$ is H, $C_{1-4}$ alkyl, $C_{2-4}$ alkenyl, $COR^2$, $COOR^{10}$, $C_{1-4}$ hydroxyalkyl or its acid ester or 2-tetrahydropyranyl ether, $C_{1-4}$ dihydroxyalkyl or its acid ester or 2-tetrahydropyranyl ether, $C_{1-4}$ halogenated alkyl; $OR^1$, $NHR^7$; each of $R^5$ $R^6$, independently, is H, CHO, $COR^1$, COOH, $COOR^9$, CN, or halogen; $R^7$ is H, $C_{1-4}$ alkyl, 2-thienyl, phenyl, mono-substituted phenyl, or di-substituted phenyl; $R^8$ is $COOR^2$, CO.CHO, $C_{1-4}$ hydroxyalkyl or its acid ester or 2-tetrahydropyranyl ether; and $R^9$ is H, $C_{1-4}$ alkyl, phenyl, mono-substituted phenyl, di-substituted phenyl, or 2-thienyl.

19 Claims, No Drawings

MEDICINAL THIOPHENE COMPOUNDS

CROSS REFERENCE TO RELATED APPLICATIONS

This application is a continuation-in-part of U.S. patent application Ser. No. 07/838,516, filed Feb. 19, 1992, now abandoned which is hereby incorporated by reference.

BACKGROUND OF THE INVENTION

The construction and the regulatory mechanisms of the immune system in mammals have been studied extensively in recent years.

Leucocytes or white blood corpuscles, which are colorless ameboid cells, occur in the blood plasma of many animals. Macrophages are a type of leucocyte which are derived from blood monocytes that have migrated into tissues and have differentiated. They are largely phagocytic and ingest particulate materials including microbes. Macrophages also play important roles in immuno-regulation, control of inflammation, regulation of metabolism, and control of growth, particularly when activated by lymphokines or immunological protein factors such as interleukin-1 ("IL-1") and tumor necrosis factor.

Macrophages are also important accessory cells for presentation of antigens to T-lymphocytes. T-lymphocytes are responsible for the development of cellular immunity. T-lymphocytes typically comprise about 70% of the total lymphocytes and about 80% of the lymph nodes.

T-lymphocytes which have been activated by IL-1 and a mitogenic agent such as concanavalin A or a specific antigen produce interleukin-2 ("IL-2"), a T-lymphocyte growth factor. IL-2, in turn, binds to specific receptors on various T-cells, activating other cells and stimulating T-cell growth and differentiation.

Interferons are another group of proteins released from T-lymphocytes that also have important immunological functions including eliciting anti-viral and anti-cancer responses. Furthermore, interferons enhance other immunological responses such as phagocytosis of macrophages, the activities of natural killer cells (lymphoid cells that kill a large range of tumor cell targets), K-cells (part of the antigen-antibody response), and T-cells; and the regulation of antibody production.

Many monothiophene derivatives are isosteres of benzene derivatives and have been investigated as human and veterinary drugs. Press, "Pharmacologically Active Compounds", *Heterocyclic in Compounds*, Vol. 44: pt. 1, Chptr. V, John Wiley and Sons (1985). Most of these monothiophene derivatives are pharmaceutically inferior to benzene derivatives and are not commercially available.

Several dithiophene derivatives have been studied to determine their pharmacological activities. For example, Zemtsova et al., *Khim Farm Zh.*, 7(8), 13 (1973); Vakhreeva et al., *Khim-Farm. Zh.*, 7(3), 24 (1973); Vakhreeva et al., *Khim-Farm. Zh.*, 6(1), 24 (1972) reported low anti-bacterial activity of certain dithiophene compounds.

The Compositae or daisy plant family includes about 1000 genera and about 20,000 species. Approximately 66 genera and 230 species have been collected in Chinese Medicine Books. These genera and species have been found to decrease body heat, detoxicate, reduce edema, relieve pain, treat tumors, and cure sores. Analysis of these particular Compositae reveals that they all contain thiophene derivatives. These thiophene derivatives are not found in other higher plants.

SUMMARY OF THE INVENTION

An aspect of this invention relates to a method of treating inflammation. The method includes the step of administering to a subject an effective amount of a compound of the following formula:

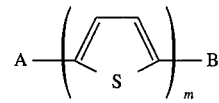

wherein m is 1–4; and each of A and B, independently, is H, $C_{1-7}$ alkyl, $C_{2-7}$ alkenyl, $C_{2-7}$ alkynyl, $(CH_2)_n CHO$, $(CH_2)_o COOH$, $C_{1-7}$ alkoxy, $C_{2-7}$ alkoxyalkyl, $C_{1-7}$ hydroxyalkyl, CN, $NO_2$, halogen, $CH(OR^1)_2$, $CO.R^1$, $NR^2R^3$ or its acid salt, $CO.NR^2R^3$, $CHR^1NR^2R^3$ or its acid salt, $CH=NR^2$, $C=CR^4$, $CR^1=CR^5R^6$, $CO.CH=CHR^7$, $CH=CHR^8$, or $COOR^9$; in which each of n and o, independently, is 0–4; $R^1$ is $C_{1-4}$ alkyl or $C_{1-4}$ acyl; each of $R^2$ and $R^3$, independently, is H, $C_{1-4}$ alkyl, or $C_{1-4}$ hydroxyalkyl; $R^4$ is H, $C_{1-4}$ alkyl, $C_{2-4}$ alkenyl, $COR^2$ $COOR^{10}$, $C_{1-4}$ hydroxyalkyl (e.g., $CH_2CH_2OH$) or its acid ester or 2-tetrahydropyranyl ether (i.e., the pharmaceutically acid ester or 2-tetrahydropyranyl ether of $C_{1-4}$ hydroxyalkyl; same below), $C_{1-4}$ dihydroxyalkyl or its acid ester or 2-tetrahydropyranyl ether (i.e., the pharmaceutically acid ester or 2-tetrahydropyranyl ether of $C_{1-4}$ dihydroxyalkyl), $C_{1-4}$ halogenated alkyl (e.g., $CH_2CH_2Cl$); $OR^1$, or $NHR^7$; each of $R^5$ and $R^6$, independently, is H, CHO, $COR^1$, COOH, $COOR^9$, CN or halogen; $R^7$ is H $C_{1-4}$ alkyl, 2-thienyl, phenyl, mono-substituted phenyl (e.g., substituted by OH, halogen, $C_{1-4}$ alkoxy, azido, amino, cyano or nitro at any position; same below), or di-substituted phenyl (e.g., substituted by OH, halogen, $C_{1-4}$ alkoxy, azido, amino, cyano or nitro at any proper position; same below); $R^8$ is $COOR^2$, CO.CHO, $C_{1-4}$ hydroxyalkyl or its acid ester or 2-tetrahydropyranyl ether; and $R^9$ is H, $C_{1-4}$ alkyl, phenyl, mono-substituted phenyl, di-substituted phenyl, or 2-thienyl.

Acids which can be used to form the above-mentioned acid salt include inorganic acids such as HCl, $H_2SO_4$, $H_3PO_4$, and organic acid such as tartaric acid, citric acid and malic acid.

Examples of acids which can be used to form the above-mentioned acid ester include, but are not limited to, $C_{1-18}$ carboxylic acid (e.g., acetic acid, palmitic acid or benzoic acid), $C_{1-18}$ sulphonic acid (e.g., cyclopentylsulphonic acid, phenanthrene-1-sulphonic acid or benezenesulphonic acid).

The structures of certain preferred compounds to be used to practice this invention can be found in Table 2, below.

The effective amount of the active compound used to practice the present invention for treating inflammation varies depending upon the manner of administration, the age and the body weight of the subject and the condition of the subject to be treated, and ultimately will be decided by the attending physician or veterinarian. Such amount of the active compound as determined by the attending physician or veterinarian is referred to herein as "effective amount".

The active compounds may be administered by any route appropriate to the condition being treated. Preferably, such a compound is injected into the bloodstream of the subject being treated. However, it will be readily appreciated by those skilled in the art that the route, such as intravenous, subcutaneous, intramuscular, intraperitoneal, nasal, oral, etc., will vary with the condition being treated and the activity of the compound being used.

The active compounds may be conveniently be presented as an ingredient of a pharmaceutical composition in unit dosage form according to any of the methods well known in the art of pharmacy. All methods include the step of bringing the active ingredient(s) into association with the carrier which constitutes one or more accessory ingredients. In general, the formulations for tablets or powders are prepared by uniformly and intimately blending the active ingredient with finely divided solid carriers, and then, if necessary as in the case of tablets, forming the product into the desired shape and size.

Other features and advantages of the present invention will be apparent from the following description of the preferred embodiments, and also from the appending claims.

DESCRIPTION OF THE PREFERRED EMBODIMENTS

The compounds used to practice this invention can be isolated or highly purified by extraction from members of the family Compositae and preferably from *Echinops grijisii*. They can also be synthesized chemically in high purity by means known to those of ordinary skill in the art including those demonstrated in the examples below.

The highly purified thiophenes of the present invention which are found to be particularly useful are bithienyl or terthienyl derivatives and intermediates. A preferred method of isolation or purification is carried out by separation via column chromatography and preferably HPLC. HPLC includes polar solvents such as ethyl acetate and the like. Surprisingly, the extract and the eluate each display significant pharmaceutical activity. For example, particularly the extract from the herb, *Echinops grijissi*, and the column chromatographic eluate by polar solvent, for example, ethyl acetate and ethanol, showed significant activities in anti-edema and interferon-inducing tests.

Highly purified thiophenes are greater than about 90% pure.

Pharmaceutical compositions within the scope of the present invention comprise these highly purified compounds in amounts effective to produce anti-inflammatory (e.g., anti-edema), anti-cancer, anti-tumor, anti-viral, anti-bacterial or immuno-regulatory activity. Immuno-regulatory activity includes, but is not limited to, stimulation, proliferation, and/or division of immune cells such as lymphocytes, particularly macrophages; the induction of interferon production; and the like.

The effective amounts of the present invention can be determined by routine experimentation well-known in the art or by establishing a matrix of dosages and frequencies and assigning a group of experimental subjects to each point in the matrix, as is well-known in the art.

Administration can be by any means known to those of ordinary skill in the art including, but not limited to oral, parenteral, transdermal, intravenous, topical, subcutaneous and the like.

Without further elaboration, it is believed that one skilled in the art can, based on the description herein, utilize the present invention to its fullest extent. The following specific example are, therefore, to be construed as merely illustrative, and not limitative of the remainder of the disclosure in any way whatsoever.

In the following examples, all parts and percentages are given by weight. $R_f$ is the ratio of the distance of migration of the compound being extracted to the distance of migration of the solvent front.

EXAMPLE 1

Synthesis of 2,2'-bithiophene 21 g of 2-iodo-thiophene was dissolved in 50 ml of DMF in 3-necks-bottle (250 ml). 10 g of Cu powder was then added into the solution and refluxed for 15 hours. Then the solution was filtered and the DMF was removed under reduced pressure. The crude product was further purified by column chromatography and both 2,2'-bithiophene (97%) as well as 2,2':5',2''-terthiophene (2%) were obtained.

Data of Spectra:
$^1$H-NMR (80 MHz CDCl$_3$): δ value 6.88 (m, 2H) 7.07 (m, 2H) 7.23 (m, 2H)

EXAMPLE 2

Synthesis of 5-formyl-2,2'-bithiophene 250 ml of DMF in 1 liter flask was added 50.2 ml of POCl$_3$ and stirred for 1 hour at 0° C. to form a complex. 83 g of 2,2'-bithiophene was dissolved in 200 ml of DMF and then added into the complex. After the solution was stirred at 10° C. for 0.5 hour, then the temperature was raised to 40 C. and stirred for 20 hours. The orange viscous product was poured into 3 l beaker and crushed ice cubes were added and stirred for 0.5 hour and then neutralized with 600 ml of 10% aqueous NaOH solution. After the solution was extracted with chloroform, washed with water and dried over anhydrous magnesium sulfate, the solvent was removed under reduced pressure and the crude product was purified by column chromatography. 90 g of product was thus obtained and the melting point thereof was 56°–57° C.

Data of Spectra:
$^1$H-NMR (80 MHz CDCl$_3$): δ value 9.70 (s, 1H) 7.47–7.60 (m, 1H) 7.10–7.30 (m, 3H) 6.90–7.06 (m, 1H)

EXAMPLE 3

Synthesis of 5-(2,2-dibromoethenyl)-2,2'-bithiophene 0.55 g of 5-formyl-2,2'-bithiophene was dissolved in 10 ml of dichloromethane. 1.95 g of PPh$_3$ and 1.23 g of CBr$_4$ were dissolved in 40 ml of dichloromethane and mixed with the 5-formyl-2,2'-bithiophene/dichloromethane solution under nitrogen gas atmosphere at 0° C. After the mixture was stirred for 1 hour and 10 ml of n-hexane was added to precipitate the triphenyl-phosphine oxide. And the reaction solution was filtered. Further, 100 ml of n-hexane was then added into the solution and the yellowish solid was obtained. The solid was further purified by column chromatography and crystallized with ethanol. The crystal product was thus obtained and the melting point thereof was 112°–113° C.

Data of Spectra:
$^1$H-NMR (80 MHz CDCl$_3$): δ value 7.50 (s,1H) 7.2–6.8 (m, 5H)

EXAMPLE 4

Synthesis of 5-ethynyl-2,2'-bithiophene

Anhydrous 5-(2,2-dibromo-ethenyl)-2,2'-bithiophene was dissolved in anhydrous THF and stirred at −78° C. After n-BuLi was added into the solution and stirred for 1 hour, the temperature was raised to 25° C. and stirred for further 1 hour. The solution was monitored by thin layer chromatography to determine whether the reaction was completed. The reaction solution was then extracted with ether and washed with water. After the solution was washed with saturated NaCl solution and dried over anhydrous magnesium sulfate.

After removal of ether, the crude product was purified by column chromatography and the oily product was obtained. The yield is 88%.

Data of Spectra:
$^1$H-NMR (90 MHz CDCl$_3$): δ value 3.2 (s, 1H) 6.8–7.2 (m, 5H)
UVmax: 330–300 nm

EXAMPLE 5

Synthesis of 5-acetyl-2,2'-bithiophene & 5,5'-diacetyl-2,2'-bithiophene (1) 8.3 g (0.05 mole) of 2,2'-bithiophene and 50 ml of acetic anhydride were mixed together and heated to reflux. Then 5 drops of phosphoric acid (85%) was added and refluxed for 4 hours. After cooled down, crushed ice cubes were added and stirred for 40 minutes. The crude product was extracted with dichloromethane and washed with water, saturated NaCl solution and dried over anhydrous magnesium sulfate. The crude product obtained after removal of solvent was purified by column chromatography and 9.46 g of product was obtained. The yield was 90% and the melting point thereof was 112°–113° C.

(2) 2.40 g of 2,2'-bithiophene was dissolved in 8 ml of acetic anhydride and refluxed under nitrogen gas atmosphere. 6 drops of phosphoric acid (85%) was added and reacted for 5 hours. The reaction mixture was poured onto 200 g of crushed ice cubes and stirred for 1 h. The solid deposited was collected and vacuum distilled, 5-acetyl-2,2'-bithiophene 1.98 g was obtained at 148° C./0.8 mm-Hg and the melting point was 112°–113° C. The residue was recrystallized from dioxane and 0.25 g of 5,5'-diacetyl-2,2'-bithiophene with melting point of 236°–9° C. was obtained.

Data of Spectra:
IR: cm$^{-1}$
a. 5-acetyl-2,2'-bithiophene 3080 aromatic C—H 1645 C=O 830, 795, 715
b. 5,5'-diacetyl-2,2'-bithiophene 1630 C=O 950, 795 bithiophene
$^1$H-NMR: δ value
a. 5-acetyl-2,2'-bithiophene 2.40 (s, 3H, COC$\underline{H}_3$) 6.86–7.53 (m, 5H, protons of thiophene)
b. 5,5'-diacetyl-2,2'-bithiophene 2.61 (s, 6H, 2-COC$\underline{H}_3$) 7.20–7.66 (m, 4H, protons of thiophene)
Mass: m/e (relative intensity)
a. 5-acetyl-2,2'-bithiophene M$^+$208 (77) M$^+$—CH$_3$ 193 (100)
b. 5,5'-Diacetyl-2,2'-bithiophene 250 (M$^+$,100) 235 (M$^+$—CH$_3$,23)

EXAMPLE 6

Synthesis of 5-ethyl-2,2'-bithiophene 0.1 g (0.48 mmole) of 5-acetyl-2,2'-bithiophene was dissolved in 1 ml of dioxane and blended with 9 ml mixture of concentrated HCl, dioxane and glacial acetic acid (3:3:3). The reaction solution was stirred for 2 hours at room temperature with excess Zn-amalgam. After the crude product was extracted with ether and neutralized with NaOH (10%), it was washed with water to neutral, dried, condensed and purified by silica gel chromatography. From the eluate of n-hexane 55 mg of product (60%) was obtained.

Data of Spectra:
$^1$H-NMR (CDCl$_3$): δ value 6.66–7.24 (m, 5H, protons of thiophene) 2.81 (q, 2H, C$\underline{H}_2$) 1.30 (t, 3H, —C$\underline{H}_3$)
IR (KBr): cm$^{-1}$ 2995 (saturated CH), 800
Mass: m/e (relative intensity)
194 (M$^+$,59), 179 (100)

EXAMPLE 7

Synthesis of 5-(1-oxo-heptyl)-2,2'-bithiophene 0.57 g (3.43 mmole) of 2,2'-bithiophene was dissolved in 10 ml of benzene. Adequate P$_2$O$_5$ was added and stirred homogeneously. 0.7 g (5.35 mmole) of n-heptanoic acid was dissolved in 10 ml of benzene and dropped into the previous mixture solution. After the reaction solution was heated at 70° C. for 2 hours, the crude product was extracted with ethyl acetate and washed with NaHCO$_3$ solution, then washed with water, dried, condensed and separated by column chromatography. n-Hexane was added as an eluant to recover the unreactive materials. The second eluant was n-hexane/ethyl acetate (10/1) and 0.28 g of yellowish platelet product (30%) was obtained. The melting point of the product was 85° C.

Data of Spectra:
$^1$H-NMR (CDCl$_3$): δ value 7.01–7.55 (m, 5H, protons of thiophene) 1.20–1.75 (m, 8H, C$\underline{H}_2$) 0.85 (t, 3H, C$\underline{H}_3$)
IR (KBr): cm$^{-1}$ 1645 (C=O)
Mass: m/e (relative intensity) 278 (M$^+$,20), 208 (40), 193 (51), 179 (100)

EXAMPLE 8

Synthesis of 5-heptyl-2,2'-bithiophene 5-(1-heptanoyl)-2,2'-bithiophene (2 g) was dissolved in 20 ml of dioxane and the mixture of concentrated HCl, dioxane and glacial acetic acid (15:20:15 ml) was added. The reaction solution was stirred for 2 hours at room temperature with excess amount of Zn-amalgam. After the crude product was extracted with ether and neutralized with NaOH (10%), it was washed with water to neutrality, dried, condensed and purified by silica gel chromatography. The eluant was n-hexane/ethyl acetate (1/20) and 0.91 g of oily product (48%) was obtained.

Data of Spectra:
$^1$H-NMR (CDCl$_3$): δ value 6.65–7.24 (m, 5H, protons of thiophene) 1.67–1.23 (m, 2H, C$\underline{H}_2$) 0.87 (t, 3H, C$\underline{H}_3$)
IR (neat): cm$^{-1}$ 2910 (CH)
Mass: m/e (relative intensity) 264 (M$^+$,24), 179 (100)

EXAMPLE 9

Synthesis of 5-formyl-5'-heptyl-2,2'-bithiophene 8 ml of dimethyl formamide (DMF) was stirred at 0° C. for 10 minutes, 1 ml of POCl$_3$ was added and then stirred for 1 hour. 0.5 g of bithienyl-heptane (3.40 mmole) dissolved in 5 ml of dimethyl formamide was added and stirred at room temperature for half an hour, then the temperature was raised to 60° C. and was further stirred for 4 hours. The reaction solution was extracted with dichloromethane, neutralized with sodium acetate, washed with water to neutrality, dried, condensed and separated by silica gel chromatography. The eluant was ethyl acetate/n-hexane (1/15). 0.86 g of slightly yellowish oily product (86%) was obtained.

Data of Spectra: $^1$H-NMR (CDCl$_3$): δ value 9.81 (s, 1H, —CHO) 6.71–7.62 (m, 4H, protons of thiophene) 2.79 (t, 2H, —C$\underline{H}_2$) 0.86 (t, 3H, C$\underline{H}_3$)
IR (neat):cm$^{-1}$ 2910 (CH) 1665 (C=O)
Mass: m/e (relative intensity) 264 (M$^+$,44), 206 (100)

EXAMPLE 10

Synthesis of 5-hydroxymethyl-5'-heptyl-2,2'-bithiophene 0.4 g of 5-formyl-5'-heptyl-2,2'-bithiophene (1.37 mmole) was dissolved in 15 ml of tetrahydrofuran (THF) and stirred at 0° C. for 10 minutes. NaBH$_4$ (0.1 g) was added at room temperature and stirred for 2 hours. Then the solution was extracted with 100 ml of ethyl acetate. The extract was washed with water, then dried and condensed. After filtration, the solid product was crystallized and further recrystallized with ethyl acetate/n-hexane mixture. The slightly yellowish solid product (0.21 g, 52%) was obtained and the melting point thereof was 59° C.

Data of Spectra:
$^1$H-NMR (CDCl$_3$): δ value 6.64–6.96 (m, 4H, protons of thiophene) 4.77–4.78 (m, 2H, OC$\underline{H}_2$) 2.75 (t, 2H, C$\underline{H}_2$) 1.23–1.76 (m, 2H, C$\underline{H}_2$) 0.87 (t, 3H, C$\underline{H}_3$)
IR (KBr): cm$^{-1}$ 3250 (OH), 1070
Mass: m/e (relative intensity) 294 (M$^+$,59), 209 (100)

EXAMPLE 11

Synthesis of 5-chloroacetyl-2,2'-bithiophene 3 g (18 mmole) of 2,2'-bithiophene was dissolved in 10 ml of CS$_2$. 7.21 g (54 mmole) of AlCl$_3$ was dissolved in 20 ml of CS$_2$. The two solutions were mixed together and stirred at room temperature. Chloroacetyl chloride (3.47 g, 30 mmole) previously dissolved in 20 ml of CS$_2$ was then dropped in slowly. After stirred for 30 minutes at room temperature, the reaction temperature was raised to 50° C. and stirred for further 2 hours and the solution was separated into two layers. The upper layer was discarded (CS$_2$). The lower layer was hydrolyzed with 10% HCl solution and extracted with dichloromethane. The extract was then washed with water, neutralized with NaHCO$_3$, dried, condensed and separated by silica gel chromatography. From n-hexane eluate, the unreacted starting material was recovered. From the eluate of n-hexane/ethyl acetate (10/1) the product was obtained.

Data of Spectra:
$^1$H-NMR (CDCl$_3$): δ value 7.65–6.88 (m, 5H, protons of thiophene) 4.55 (s, 2H, OC$\underline{H}_2$, Cl)
IR (KBr): cm$^{-1}$ 1670 (C=O), 1450, 1220

EXAMPLE 12

Synthesis of 5-(1-hydroxypropyl)-2,2'-bithiophene 3 g of 5-formyl-2,2'-bithiophene was dissolved in THF (50 ml) and 9.3 ml of ethyl-magnesium bromide Grignard reagent was dropped in slowly under nitrogen gas atmosphere in ice bath with stirring for 1 hour. The mixture was then stirred at room temperature and was monitored by thin layer chromatography to determine whether the reaction was completed. After the reaction was completed, 30 ml of water and 200 ml of ethyl acetate were added. The ethyl acetate extract was further purified by column chromatography. From the eluate of ethyl acetate/n-hexane (1/9), slightly yellowish oil was obtained.

Data of Spectra:
$^1$H-NMR (CDCl$_3$): δ value 7.16–6.63 (m, 5H, protons of thiophene) 4.78–4.73 (t, 1H, —C$\underline{H}$(OH)CH$_2$CH$_3$) 1.92–1.79 (m, 2H, —C$\underline{H}_2$CH$_3$) 0.98–0.90 (t, 3H, —C$\underline{H}_3$)
IR (NaCl): cm$^{-1}$ 3400 (OH), 2950 (CH)

EXAMPLE 13

Synthesis of 5-(1-propenyl)-2,2'-bithiophene 1 g of 5-hydroxypropyl-2,2'-bithiophene was dissolved in 20 ml of benzene, followed by adding 0.1 g of p-toluenesulfonic acid. The mixture was then stirred at room temperature for 2 hours while monitoring by thin layer chromatography. After completion of reaction, 30 ml of water and 100 ml of ethyl acetate were then added to the mixture. The ethyl acetate extract was further purified by column chromatography. The eluant was ethyl acetate/n-hexane (1/9). The slightly yellowish liquid product was thus obtained.

EXAMPLE 14

Synthesis of 5-carboxy-2,2'-bithiophene 35 ml of NaOCl solution was heated to 55° C. and 5-acetyl-2,2'-bithiophene was then added and stirred at 60°–70° C. for 2 hours. Then the reaction solution was cooled by ice bath and aqueous Na$_2$S$_2$O$_4$ solution was added for removing the residual NaOCl. The reaction mixture was acidified by HCl(aq) and filtered to obtain golden product. The product was further recrystallized with 95% ethanol. The melting point of the product was 183–184%.

Data of Spectra:
UVmax: 320–335 nm
$^1$H-NMR (400 MHz d-acetone): δ value 7.7–7.1 (5H) no —COOH signal in d-acetone solvent
IR: cm$^{-1}$ 2000–3600 —COOH 1678 —CO—
Mass : m/e 210 (M$^+$)

EXAMPLE 15

Synthesis of 5-iodo-2,2'-bithiophene 33.2 g of 2,2'-bithiophene was dissolved in 50 ml of ethanol and I$_2$/EtOH (20.3 g/220 ml) was added. Then HIO$_3$/H$_2$O (12 g/20 ml) were added slowly during 2 hours with stirring. The mixture was stirred for further 3 hours and the ethanol was evaporated. The residue was extracted with dichloromethane and dried over anhydrous magnesium sulfate. After the solvent was removed, the crude product was vacuum distilled to give 5-iodo-2,2'-bithiophene 36.8 g (105°–110° C./0.1 mm-Hg). The yield is 65–70%. The residue was purified by silica column chromatography and yielded 5.36 g of 5,5'-diiodo-2,2'-bithiophene (6.4%) with melting point of 170° C.

EXAMPLE 16

Synthesis of 5-hydroxymethyl-2,2'-bithiophene 20 g of 5-formyl-2,2'-bithiophene was dissolved in 50 ml of methanol, followed by adding NaBH$_4$ and stirring until bubbling stopped. The reaction was monitored by thin layer chromatography to determine whether the reaction was completed. After the methanol was removed under reduced pressure and the reaction solution was extracted with dichloromethane, the solution was washed with saturated NaCl solution, dried over anhydrous magnesium sulfate, condensed and 20.10 g of product (melting point 52°–53° C., 99%) was thus obtained.

Data of Spectra:
UVmax: 300–320 nm
IR: cm$^{-1}$ 3000–3500 —CH
$^1$H-NMR (400 MHz DMSO): δ value 4.5–4.6 (d, 2H) 5.5–5.52 (t, 2H) 6.6–7.4 (5H)
Mass: m/e 196 (M$^+$)

EXAMPLE 17

Synthesis of 5-(N-phenyliminomethylidene)-2,2'-bithiophene 5.0 g of 5-formyl-2,2'-bithiophene was dissolved in 45 ml of benzene. 2.4 ml of aniline was added and refluxed for 24 hours at 85° C. 6.9 g of crude product was obtained after removal of solvent under reduced pressure and the purer product could be obtained by recrystallization with ethanol.

Data of Spectra:
$^1$H-NMR (400 MHz CDCl$_3$): δ value 6.97–7.33 (m, 10H) 8.44 (s, 1H)

EXAMPLE 18

Synthesis of 5-(N-phenylaminomethyl)-2,2'-bithiophene 6.94 g of 5-(N-phenyliminomethylidene-2,2'-bithiophene was dissolved in 250 ml of methanol, followed by adding NaBH$_4$ and stirring until bubbling stopped. After the methanol was removed under reduced pressure, the reaction residue was extracted with dichloromethane. The solution was then washed with saturated NaCl solution, dried over anhydrous magnesium sulfate, condensed under reduced pressure and 6.41 g of yellowish solid (91.6%) was thus obtained.

Data of Spectra:
$^1$H-NMR (400 MHz CDCl$_3$): δ value 4.49 (b, 1H of NH) 4.80 (s, 2H) 6.69–7.26 (m, 10H)
Mass: m/e 271 (M$^+$)

EXAMPLE 19

Synthesis of 5-(N-2,3-dihydroxypropyliminomethylidene)-2,2,'-bithiophene 5.74 g of 5-formyl-2,2'-bithiophene was dissolved in 60 ml of benzene, followed by dropping in excess 2,3-dihydroxy-propenylamine and refluxed at 85° C. for 5 hours with molecular sieves. Then the benzene was evaporated under reduced pressure and 9.68 g of residual solid was obtained. A yellowish product (85%) could be further recrystallized from ethanol.

Data of Spectra:
$^1$H-NMR (400 MHz CDCl$_3$): δ value 8.3 (s, 1H) 7.33–6.99 (m, 5H) 3.97 (m, 1H) 3.77 (m, 2H) 3.70 (m, 2H) 2.5–3.3 (b, 2H)
Mass: m/e 67 (M$^+$)

EXAMPLE 20

Synthesis of 5-(N-2,3-dihydroxypropylaminomethyl)-2,2'-bithiophene 5-(N-2,3-dihydroxypropyliminomethylidene)-2,2'-bithiophene was dissolved in 50 ml of methanol and stirred in ice bath. NaBH$_4$ was added until bubbling stopped. After the methanol was removed under reduced pressure and the residue was extracted with dichloromethane. The extract was washed with saturated NaCl solution, dried over anhydrous magnesium sulfate and condensed under reduced pressure. The crude yellow glue-like product was thus obtained.

Data of Spectra:
Mass: m/e 269 (M$^+$)

EXAMPLE 21

Synthesis of 5-(3-oxo-3-thienyl-1-propenyl)-2,2'-bithiophene 0.97 g of 5-formyl-2,2'-bithiophene was dissolved in 10 ml of ethanol and the temperature thereof was maintained at 5°–10° C. in ice bath. After 0.62 ml of 2-acetyl-2,2'-bithiophene was added in and stirred for 10 minutes, orange solid was deposited. After 12 hours, it was decomposed with 25 ml of water. The crude product was collected and recrystallized from ethanol. 1.33 g of product was thus obtained and the melting point thereof was 129°–130° C. (yield: 86.1%).

Data of Spectra:
Mass: m/e 302 (M$^+$)

EXAMPLE 22

Synthesis of 5-(1-oxo-3-thienyl-2-propenyl)-2,2'-bithiophene 1.1 g of 5-acetyl-2,2'-bithiophene was dissolved in 35 ml of ethanol, followed by adding 0.6 ml of 2-formyl-thiophene and KOH solution (KOH: H$_2$O : ethanol=0.5 g: 1 ml: 5 ml). The color of the solution was turned into dark brown. Additional 0.1 ml of 2-formyl-thiophene was added to complete the reaction. The reaction solution was monitored by thin layer chromatography to determine whether the reaction was completed. The reaction mixture was kept in a refrigerator overnight. Decomposed with water and the crude product was collected. After the product was recrystallized from ethanol, 1.27 g of product was thus obtained and the melting point thereof was 135°–136° C. (yield: 84.1%).

Data of Spectra:
Mass: m/e 302 (M$^+$)

EXAMPLE 23

Synthesis of 5-(3-p-hydroxyphenyl-3-oxo-1-propenyl)-2,2,'-bithiophene 1.94 g of 5-formyl-2,2'-bithiophene was dissolved in 15 ml of ethanol. Then 1.36 g of p-hydroxyphenyl-methyl-ketone was added in, followed by adding KOH (1 g dissolved in H$_2$O and ethanol), the color of the mixture turned into orange. Some crude crystals were crystallized and dissolved later. The reaction solution was placed in a refrigerator overnight. The next day, it was decomposed with ice water and 2 ml of acetic acid were added. The crude product was collected and recrystallized from ethanol, 0.52 g of golden crystal product was thus obtained and the melting point thereof was 202°–205° C.

Data of Spectra:
Mass: m/e 312 (M$^+$)

EXAMPLE 24

Synthesis of 5-(3-(3-methoxyl-p-hydroxyphenyl)-1-oxo-2-propenyl)-2,2'-bithiophene 1 g of vanillin and 1.5 g of 3,4-dihydro-pyrane were mixed in a flask. 0.2 g of p-toluene-sulfonic acid was added and stirred. After the reaction was completed, pyrane was removed under reduced pressure and the reaction solution was dissolved in 10 ml of absolute ethanol. Then 1.22 g of 5-acetyl-2,2'-bithiophene was added, followed by adding 1 ml KOH (40%) of ice cold solution. After kept in a refrigerator overnight, the reaction mixture was decomposed with 50 ml of ice water and 2 ml of acetic acid. The reaction solution was then extracted by ethyl acetate and the black oily product was obtained. The oily product was purified by column chromatography. The eluate of ethyl acetate/n-hexane was 1/19; 1/15; 1/13 by order. From the later fraction 0.24 g of purified product was obtained after recrystallization from ethyl acetate. The melting point was 166°–8° C.

Data of Spectra:
Mass: m/e 342 (M$^+$)

EXAMPLE 25

Synthesis of 2-(3-oxo-3-thienyl-1-propenyl)thiophene 11 ml of 2-acetyl-thiophene and 11 ml of 2-formyl-thiophene were dissolved in 10 ml of ethanol and followed by adding 4 ml of 60% KOH solution with stirring. After kept in a refrigerator overnight, the reaction mixture was decomposed with ice water to give yellowish solid. The solid was dissolved in ethanol and filtered. The melting point of the undissolved white crystal was 248° C. From the filtrate 9.08 g of pure crystal with melting point of 95° C. was obtained.

EXAMPLE 26

Synthesis of 5-(4-hydroxy-4-methyl-3-oxo-1-pentenyl)-2,2'-bithiophene 3.92 g of 5-formyl-2,2'-bithiophene was dissolved in 37 ml of ethanol. 3 ml of 3-hydroxy-3-methyl-2-butanone was then added into the solution and the temperature thereof was maintained at 15° C. After 5 ml of 60% KOH solution was dropped in and the temperature thereof raised to 17° C., some crystals appeared gradually and the color thereof changed from yellow to orange. After completion of the reaction, the solid was filtered and recrystallized with ethanol/$H_2O$ (1:1), 5.12 g of crystal (melting point was 92.5° C.) was thus obtained.

Data of Spectra:
$^1$H-NMR (CDCl$_3$): δ value 7.87 (d, 1H, CH=CH—CO) 7.20–7.02 (m, 5H, protons of thiophene) 6.72 (d, 1H, CH=CH—CO—) 1.43 (s, 6H, —(CH$_3$)$_2$)
UVmax: 393 nm
IR: cm$^{-1}$ 3410 —OH—1665 —CO—1580 —C=C— 1460 —C=C—

EXAMPLE 27

Synthesis of 5-(3-oxo-1-butenyl)-2,2'-bithiophene 3.39 g of 5-formyl-2,2'-bithiophene and 2 ml of acetone was dissolved in 50 ml of ethanol. The temperature of the reaction solution was controlled at 12° C. and diluted KOH solution was dropped in. After the temperature of the mixture raised to 16° C. and the color thereof changed from dark yellow to orange red. After completion of the reaction in refrigerator for overnight, the reaction mixture was decomposed with water. The solid collected was recrystallized from alcohol. A yellowish crystal (2.23 g) was thus obtained. The melting point of the product was 204° C.

Data of Spectra:
Mass: m/e 234 (M$^+$) 219 (M$^+$—CH$_3$)

EXAMPLE 28

Synthesis of 5-(4-dimethoxy-3-oxo-1-butenyl)-2,2'-bithiophene 4 g of 5-formyl-2,2'-bithiophene was dissolved in 120 ml of ethanol. 3 ml of pyruvic aldehyde dimethyl acetate was then added and the temperature of the solution was maintained at 16 C. 50% KOH solution was dropped in slowly and the color thereof changed from yellow-brown to dark green and further to dark brown. After kept overnight in a refrigerator the reaction mixture was decomposed with ice water. The solid collected was separated by silica gel chromatography. The eluate with ethyl acetate/n-hexane (1/9) gave 1.88 g yellow crystal. The melting point of the product was 74° C.

Data of Spectra:
$^1$H-NMR (CDCl$_3$): δ value 7.82 (d, 1H, —CH=CH—) 7.27–7.03 (m, 5H, protons of thiophene) 6.77 (d, 1H, CH=CH—) 3.43 [s, 6H, (OCH$_3$)2]
Mass: m/e 294 (M$^+$) 2 19 [M$^+$—CH (OCH$_3$)$_2$]

EXAMPLE 29

Synthesis of 5-(4-dimethoxy-3-hydroxy-1-butenyl)-2,2'-bithiophene 50 mg of 5-(4-dimethoxy-3-oxo-1-butenyl)-2,2'-bithiophene was dissolved in 2.52 ml of THF and stirred at room temperature. 10 mg of NaBH$_4$ was then added and stirred for 1 hour at room temperature. After ethyl acetate and distilled water were added, the ethyl acetate layer was separated and dried over anhydrous magnesium sulfate. The solvent was removed and separated by column chromatography to obtain a greenish oily product.

Data of Spectra:
$^{13}$C-NMR (400 MHz CDCl$_3$): δ value 55.11, 55.73, 71.83, 123.71, 123.88, 124.46, 125.94, 126.42, 127.00, 127.00, 127.87, 136.25, 137.49, 140.91
IR: cm$^{-1}$ 3400 (—OH), 2950 (—CH), 1070 (—C—O)

EXAMPLE 30

Synthesis of 5-(3,4-dioxo-1-butenyl)-2,2'-bithiophene 5-(4-dimethoxy-3-oxo-1-butenyl)-bithiophene was dissolved in 40 ml of ethanol under nitrogen gas atmosphere and dilute HCl solution (20 ml, 3N) was added. After the reaction solution was refluxed for 4 hours, 400 ml of ethyl acetate was added. The extract was then washed with water, NaHCO$_3$ solution repeatedly and was dried over anhydrous magnesium sulfate. After the solution was condensed and purified by column chromatography, the dark orange liquid product was obtained.

EXAMPLE 31

Synthesis of 5-(3,4-dihydroxy-1-butenyl)-2,2'-bithiophene 0.5 g of 5-(3,4-dioxo-1-butenyl)-2,2'-bithiophene and 0.2 g of NaBH$_4$ were dissolved in 10 ml of tetrahydrofuran and stirred at room temperature for 2 hours. Each 100 ml of ethyl acetate and distilled water were added into the reaction solution for extraction. The ethyl acetate layer was washed with water and dried over anhydrous magnesium sulfate. After condensation, the product was separated by column chromatography. The eluate of ethyl acetate/n-hexane (3/7) yielded slightly yellowish crystal and the melting point thereof was 96°–98° C.

Data of Spectra:
$^1$H-NMR (400 MHz, CDCl$_3$): δ value 3.60–3.74 (dd, 2H, —CH$_2$OH) 4.40 (m, 1H, —CH (OH)) 5.98–6.06 (dd, 1H, C=CH—) 7.20–7.26 (d, 1H, —CH=C) 6.86–7.17 (m, 5H, protons of thiophene)
IR (KBr): cm$^{-1}$ 3326, 3076, 1462, 1423, 1122, 960, 790, 688
Mass (12 ev): m/e (relative intensity) 252 (M$^+$, 91), 233(30), 221(100), 204(24), 176(15)

EXAMPLE 32

Synthesis of 5-(4-dimethoxy-3-oxo-1-butenyl)-2,2':5',2"-terthiophene 0.63 g of 5-formyl-2,2':5'2"-terthiophene and 0 32 g of pyruvic aldehyde dimethyl acetal were dissolved in 100 ml of ethanol. 0.24 g of NaOH (10%) solution was dropped into the reaction solution slowly and the color thereof changed from yellow to dark orange. After the solution was stirred overnight, the ethanol was removed under reduced pressure and 100 ml of dichloromethane was added for extraction. The crude product was separated by column chromatography. The yield of the product was 50% and the melting point thereof was 125°–126° C.

Data of Spectra:
$^1$H-NMR (400MHz CDCl$_3$): δ value 3.40 (s, 6H, 2—OCH$_3$) 4.46 (s, 1H, —CH(OCH$_3$)$_2$) 6.69–6.73 (d, 1H, —CH=) 7.74–7.78 (d, 1H, =CH—) 6.94–7.19 (m, 7H, protons of thiophene)

$^{13}$C-NMR (400 MHz CDCl$_3$): δ 54.37, 54.37, 119.04, 124.12, 124.37, 124.49, 125.00, 125.63, 127.96, 133.91, 135.12, 136.62, 137.04, 137.83, 138.63, 141.03, 193.30

EXAMPLE 33

Synthesis of 2,2':5',2''-terthiophene 1.24 g of Mg turning was added into 3-necked-flask (250 ml) previously dried in an oven, and equipped with a funnel containing 8.2 g of thienyl bromide in 100 ml of dry ether, thermometer and condenser connected with a nitrogen gas tubing. Before the thienyl bromide/dry ether solution was dropped in, the whole flask was dried with nitrogen stream for 15 minutes. 30 ml of dry ether, 1 drop of iodomethane and 1 particle of iodine were added. Then thienyl bromide/dry ether solution was dropped in gradually. The thienyl magnesium bromide was obtained after stirred for 30 minutes. Another 250 ml 3-necked flask equipped with dropping funnel, thermometer and condenser was set with 0.07 g of NiCl$_2$ (dppp), 40 ml of dry ether and 5.0 g of 5,5'-dibromo-2,2'-bithiophene. The previously prepared thienyl Grignard Reagent was dropped into the later flask during 30 minutes. After refluxed for 6 hours, the flask was cooled in ice bath and 20 ml of HCl (2N) solution was added slowly. The ether layer was separated from the water layer. The water layer was further extracted with ether and the combined ether layer was washed with Na$_2$CO$_3$ solution and dried over anhydrous magnesium sulfate. The pure product was obtained by silica gel column chromatography and the melting point thereof was 94°–95° C. (yield was 93.8%).

Data of Spectrum:

UVmax: 305 nm bithiophene 355 nm terthiophene 380 nm tetrathiophene $^1$H-NMR (CDCl$_3$ α-T): δ 6.999–7.01 (dd, 2H, J=4.5) 7.06 (s, 2H, S) 7.15 (d, 2H, J=4) 7.21 (dd, 2H, J=5)

EXAMPLE 34

Synthesis of 5-formyl-2,2':5',2''-terthiophene & 5,5''-diformyl-2,2':5',2''-terthiophene (1) 15 ml of DMF and 1.03 ml of POCl$_3$ were mixed together and stirred under nitrogen gas atmosphere for few minutes. 2.48 g of α-T/DMF solution was dropped into the mixture and heated to 70° C. The temperature of the mixture was raised to 110° C. and maintained for 2.5 hours. After decomposed with ice water and neutralized with weak base, 100 ml of chloroform was added for extraction. The extract was dried over anhydrous magnesium sulfate and the solvent was removed under reduced pressure. The crude product was separated by silica gel chromatography. a. In the eluate of chloroform/n-hexane (1/4), 1.94 g of 5-formyl-2,2':5',5''-terthiophene was obtained and the melting point thereof was 141°–142° C. (yield was 74.2%). b. In the eluate of chloroform/n-hexane/ethyl acetate (38/1/1), 0.13 g of 5,5''-diformyl-2,2':5',2''-terthiophene was obtained and the melting point thereof was 219°–220° C. The yield of the product was 4.3% and the recovered α-T was 0.13 g.

Data of Spectrum:

UVmax: 400 nm 5-formyl-2,2':5',2''-terthiophene 410 nm 5,5''-diformyl-2,2,:5',2''-terthiophene IR (KBr): cm$^{-1}$ 5-formyl-2,2':5',2''-terthiophene 1649 —C=O 2930 —C—H 5,5''-diformyl-2,2':5',2''-terthiophene 1649 C=O $^1$H-NMR (CDCl$_3$): δ 5-formyl-2,2':5',2''-terthiophene 9.86 (s, 2, —CHO) 7.67 (d, 1H, J$_{3-4}$=4) 7.25 (d, 2H, J=4.5) 7.21 (d, 2H, J=4) 7.10 (d, 1H, J=4) 7.02 (t, 1H, J=–4) 5''-diformyl-2,2':5',2''-terthiophene 9.86 (S, 2, —CHO) 7.67 (d, 2H, J$_{3-4}$=4) 7.30 (S, 2H) 7.27 (d, 2H, J=4)

Mass : m/e 276 (M$^+$) 5-formyl-2,2':5',2''-terthiophene 304 (M$^+$) 5,5''-diformyl-2,2':5',2''-terthiophene (2) 1 g of 5-iodo-2-thiophenecarboxaldehyde was dissolved in 200 ml of acetonitrile. 0.7 g of bithiophene was added into the solution under nitrogen gas atmosphere for 1 hour and irradiated under 100 W mercury-vapor lamp light for 12 hours. The solution was monitored by thin layer chromatography. At this stage, about 60% product was generated. The acetonitrile was removed from the reaction solution under reduced pressure and CH$_2$Cl$_2$ was added for extraction. After the extract was filtered through silica gel layer and separated by column chromatography, starting material was recovered from the eluate of ethyl acetate/n-hexane 1/9 fraction and 5-formyl-2,2':5',2''-terthiophene was obtained from the eluate of ethyl acetate/n-hexane 3/7 fraction respectively.

EXAMPLE 35

Synthesis of 5-acetyl-2,2':5,2''-terthiophene & 5,5''-diacetyl-2,2':5',2''-terthiophene The mixture of 4.96 g of terthienyl and 2.5 ml of acetic anhydride was heated to 110° C and 8 drops of 85% phosphoric acid was dropped into the mixture and stirred for 4 hours. After the temperature of the reaction solution was lowered to room temperature, it was poured into ice water and neutralized with NaHCO$_3$. The reaction solution was filtered, washed with water and separated by silica gel chromatography. From the eluate of ethyl acetate/n-hexane= 2/8 fraction 3.6 g of 5-acetyl-α-terthienyl was obtained. The yellow solid product was recrystallized by chloroform/n-hexane and the melting point thereof was 175°–176° C. The solubility of diacetyl-α-terthienyl was very low but could be purified by TLC of the less soluble residue. The melting point of the product was 248°–250° C.

Data of Spectra:

UVmax: 390 nm 5-acetyl-2,2':5',2''-terthiophene 410 nm 5,5''-diacetyl-2,2':5',2''-terthiophene IR (KBr)(5-acetyl-2,2':5',2''-terthiophene): cm$^{-1}$ 3130, 3000 —CH$_3$, aromatic C—H 1618 —C=O $^1$H-NMR (CDCl$_3$): δ value 5-acetyl-2,2':5',2''-terthiophene 2.54 (3H, —CH$_3$) 7.02 (m, 1H) 7.10 (d, 1H, J=3) 7.13 (d, 1H, J=3) 7.20 (t, 2H, J=4) 7.25 (d, 1H, J=3) 7.57 (d, 1H, J=3)

Mass: m/e 5-acetyl-2,2':5',2''-terthiophene 290 (M$^+$, 100) 275 (M$^+$—CH$_2$OH, 25)

EXAMPLE 36

Synthesis of 5-methyl-2,2':5',2''-terthiophene 0.5 g of 5-formyl-2,2':5',2''-terthiophene was dissolved in a mixture of HCl, dioxane and glacial acetic acid (1:2:1), followed by adding 5 g of Hg-Zn catalyst. After reacting for 3 hours, the solution was monitored by thin layer chromatography to determine whether the reaction was completed. 200 ml of ethyl acetate was then added and washed with aqueous K$_2$CO$_3$ solution. The extract was further separated by column chromatography and the eluant was n-hexane. The yellowish crystal was obtained by adding little amount of ethyl acetate into the condensed hexane solution for recrystallization. The melting point of the product was 93°–94° C. (yield: 90%).

Data of Spectra:

$^1$H-NMR (CDCl$_3$): δ value 7.19–6.64 (m, 7H, protons of thiophene) 2.46 (s, 3H, —CH$_3$)

IR (KBr): cm$^{-1}$ 2900 (OH), 1430 (conjugative C=C)

Mass: m/e (relative intensity) 262 (M$^+$, 100), 249(17), 131(12)

EXAMPLE 37

Synthesis of 5-hydroxymethyl-5"-methyl-2,2':5',2"-terthiophene 0.2 g of 5-formyl-5"-methyl-2,2':5',2'-terthiophene was dissolved in 50 ml of ethanol. NaBH$_4$ (0.1 g) was added at room temperature and stirred for 30 minutes. The solution was monitored by thin layer chromatography to determine whether the reaction was completed, then 150 ml of ethyl acetate and 50 ml of water were added therein. The ethyl acetate extract was washed with water, dried and purified by silica gel column chromatography. The slightly yellowish crystal was thus obtained and melting point thereof was 126°–128° C. The yield was almost quantitative.

Data of Spectra:

$^1$H-NMR (CDCl$_3$): δ value 7.09–6.72 (m, 6H, protons of thiophene) 4.87–4.85 (d, 2H, —C$\underline{H}_2$OH) 2.54 (s, 3H, —CH$_3$) IR (KBr): cm$^{-1}$ 3300 (—OH), 2900(C—H), 1450 (conjugative C=C) 1030, 1000, 800

Mass: m/e (relative intensity) 292 (M$^+$, 100), 275 (79), 258 (11)

EXAMPLE 38

Synthesis of 5-propanoyl-2,2':5',2"-terthiophene 5 g of 2,2':5',2"-terthiophene was dissolved in 250 ml of benzene. 3.1 g of P$_2$O$_5$ was added into the solution and 1.6 g of propionic acid was dropped in slowly at room temperature and then heated to reflux. And the solution was monitored by thin layer chromatography to determine whether the reaction was completed. If the reaction was incomplete, more P$_2$O$_5$ was added. 50 ml of water and K$_2$CO$_3$(aq) were added into the reaction mixture and extracted with ethyl acetate. Further purification by column chromatography, the eluate of ethyl acetate/n-hexane (1/19) yellowish solid was obtained. The yellowish cotton-like crystal was obtained by recrystallization from n-hexane/ethyl acetate (1/19). The melting point of the product was 136°–137° C. (yield: 20%).

Data of Spectra:

$^1$H-NMR (CDCl$_3$): δ value 7.58–7.00 (m, 7H, protons of thiophene) 2.92–2.86 (q, 2H, —C$\underline{H}_2$CH$_3$) 1.24–1.20 (t, 3H, —CH$_2$C$\underline{H}_3$)

IR (KBr): cm$^{-1}$ 2900 (—CH), 1650 (conjugative C=O), 1440 (conjugative C=C), 1230, 1060, 790

Mass: m/e (relative intensity) 304 (M$^+$, 73), 275 (100), 247 (21), 203 (59)

EXAMPLE 39

Synthesis of 5-(1-hydroxy-propyl)-2,2':5',2"-terthiophene (1) 0.6 g of 5-propanoyl-2,2':5',2"-terthiophene was dissolved in ethanol (150 ml) and heated to be dissolved completely. NaBH$_4$ (0.1 g) was added at room temperature and stirred for 3 hours. The solution was monitored by thin layer chromatography to determine whether the reaction was completed. After 50 ml of water was added, the ethanol was removed under reduced pressure. The yellowish green solid thus obtained and the melting point thereof was 89°–90° C. The yield was almost quantitative.

Data of Spectra:

$^1$H-NMR (CDCl$_3$): δ value 7.20–6.84 (m, 4H, protons of thiophene) 4.80–4.77 (t, 1H, —CH(OH)—C$\underline{H}_2$CH$_3$) 1.93–0.94 (t, 3H, —CH$_2$CH$_3$)

IR (KBr): cm$^{-1}$ 3400(—OH), 2900(—CH), 1450 (conjugative C=C)

Mass: m/e (relative intensity) 304 (M$^+$, 58), 277 (100)

(2) 3.5 g of 5-formyl-2,2':5',2"-terthiophene was dissolved in 200 ml of anhydrous THF under nitrogen stream. 7.9 ml of ethyl Grignard reagent was dropped in slowly under ice bath temperature and stirred at 0° C. for 1 hour. The reaction mixture was then heated to 70° C. in oil bath for 4 hours. The solution was monitored by thin layer chromatography to determine whether the reaction was completed. 50 ml of water and 300 ml of ethyl acetate were added and the ethyl acetate extract was purified by column chromatography. From the eluate of ethyl acetate/n-hexane (1/9) fraction, yellow solid was obtained and recrystallized to give granulate crystal. The melting point of the product was 89°–90° C. and the yield was about 70%.

EXAMPLE 40

Synthesis of 5-propenyl-2,2':5',2"-terthiophene 0.8 g of 5-(1-hydroxypropyl)-2,2':5',2"-terthiophene was dissolved in a mixture containing benzene and methanol (50 ml: 50 ml). 5 ml of HCl (2N) was then added at room temperature, heated to 50° C. and stirred for 1 hour. The solution was monitored by thin layer chromatography to determine whether the reaction was completed. Each 250 ml of ethyl acetate and water were added and the organic layer was separated and washed with water. After removal of solvent the crude product was purified by column chromatography. The eluate of n-hexane gave the pure product.

Data of Spectra:

$^1$H-NMR (CDCl$_3$): δ value 7.19–6.72 (m, 7H, protons of thiophene) 6.47–6.42 (dd, 1H, —C$\underline{H}$=CHCH$_3$) 6.08–5.99 (m, 1H, —CH=C$\underline{H}$CH$_3$) 1.86–1.83 (d, 3H, =CHC$\underline{H}_3$)

IR (KBr): cm$^{-1}$ 2850 (CH), 1430 (conjugative C=C)

EXAMPLE 41

Synthesis of 5-formyl-5"-propenyl-2,2':5',2"-terthiophene 2 ml of POCl$_3$ was added into dimethyl formamide (30 ml) slowly under nitrogen gas atmosphere in ice bath and stirred for 1 hour. 20 ml of dimethyl formamide solution of 5-(1-propenyl)-2,2':5',2"-terthiophene (0.8 g) was dropped in slowly. The mixture was stirred for half an hour at room temperature, then the temperature was raised to 60° C. and was further stirred for 2 hours. The solution was monitored by thin layer chromatography to determine whether the reaction was completed. The reaction solution was poured into sodium carbonate ice water solution. Then the solution was extracted with 300 ml of ethyl acetate and the extract was washed with water and dried over magnesium sulfate. After evaporation of solvent, the residual solid was purified by column chromatography. From eluate of ethyl acetate/n-hexane (1/9), the orange solid product was obtained and the melting point of the product was 146°–148° C. The yield was about 70%.

Data of Spectra:

$^1$H-NMR (CDCl$_3$): δ value 9.50 (s, 1H, —CHO) 7.65–6.74 (m, 6H, protons of thiophene) 6.47–6.43 (dd, 1H, —C$\underline{H}$=CHCH$_3$) 6.11–6.02 (m, 1H, —CH=C$\underline{H}$CH$_3$) 1.86–1.84 (d, 3H, C$\underline{H}_3$)

IR (KBr): cm$^{-1}$ 2900 (CH), 1660 (conjugative C=O), 1440 (conjugative C=C)

Mass: m/e (relative intensity) 316 (M$^+$, 100), 149 (58)

EXAMPLE 42

Synthesis of 5-hydroxymethyl-5"-propenyl-2,2':5',2"-terthiophene 0.4 g of 5-formyl-5"-(1-propenyl)-2,2':5',2"-terthiophene (0.4 g) was dissolved in 50 ml ethanol. 0.1 g of $NaBH_4$ was added at room temperature and stirred for 2 hours. The solution was monitored by thin layer chromatography to determine whether the reaction was completed. 50 ml $H_2O$ was added and the ethanol was removed under reduced pressure. Then the solid precipitate was extracted with 200 ml of ethyl acetate. The residual solid on removal of solvent was further purified by column chromatography. The eluant was ethyl acetate/n-hexane (3/7). The yellowish solid product was obtained and melting point thereof was 132°–134° C. The yield was nearly quantitative.

Data of Spectra:

$^1$H-NMR ($CDCl_3$): δ value 7.20–6.60 (m, 6H, protons of thiophene) 6.46–6.42 (dd, 1H, —C$\underline{H}$=CH—CH$_3$) 6.06–6.01 (m, 1H, —CH=C$\underline{H}$—CH$_3$) 4.79–4.78 (d, 2H, —C$\underline{H}_2$OH) 1.85–1.84 (d, 3H, —C$\underline{H}_3$)

IR (KBr): $cm^{-1}$ 3400 (OH), 2900 (CH), 1440 (conjugative C=C)

Mass: m/e (relative intensity) 318 ($M^+$, 100), 301 (26), 261 (40)

EXAMPLE 43

Synthesis of 5-(2-chloroacetyl)-2,2':5',2"-terthiophene 1 g (4 mmole) of 2,2':5',2"-terthiophene was dissolved in 20 ml of $CS_2$. 3 g of anhydride $AlCl_3$ was dissolved in 20 ml of $CS_2$ and combined with the previous solution immediately. Under stirring at room temperature, 0.55 ml (6.8 mmole) of chloroacetyl chloride was added into the mixture and stirred for 2 hours until the reaction was completed. The solution was separated into two layers. The upper layer was discarded ($CS_2$). The lower layer was hydrolyzed with 10% HCl and extracted with dichloromethane. The reaction solution was then washed with water, neutralized with $NaHCO_3$, dried, condensed and separated by silica gel chromatography. From the eluate of n-hexane/ethyl acetate (8/1) the product was obtained. This was further recrystallized from dichloromethane/ethyl acetate/n-hexane mixture gave 0.76 g of pure product (58%, dark yellow platelet crystal, melting point: 166°–168° C.).

Data of Spectra:

$^1$H-NMR ($CDCl_3$): δ value 7.01–7.76 (m, 7H, protons of thiophene) 4.54- (s, 2H, —COCH$_2$Cl)

IR (KBr): $cm^{-1}$ 1670 (C=O), 1210

Mass: m/e (relative intensity) 324 ($M^+$, 52), 275 (100), 247 (22)

EXAMPLE 44

Synthesis of 5-(2-chloro-1-hydroxyethyl)-2,2':5',2"-terthiophene 0.25 g (0.8 mmole) of 5-(2-chloro-acetyl)-2,2':5',2"-terthiophene was dissolved in 20 ml of THF and little excess of $NaBH_4$ was added. After stirred for 2 hours, the solvent was removed under reduced pressure and the crude product was separated by silica gel chromatography. From the eluate of ethyl acetate/n-hexane (1/10), 0.1 g of yellowish solid product was thus obtained and the melting point thereof was 105° C.

Data of Spectra:

$^1$H-NMR ($CDCl_3$): δ value 6.93–7.15 (m, 7H, protons of thiophene) 5.09–5.16 (m, 1H, —CH$_2$Cl) 3.74–3.81 (m, 2H, CH(OH)CH$_2$Cl)

IR (KBr): $cm^{-1}$ 3350 (OH), 790

Mass: m/e (relative intensity) 326 ($M^+$, 44), 308 (31), 277 (100)

EXAMPLE 45

Synthesis of 5-hydroxymethyl,-2,2':5',2"-terthiophene 0.5 g of 5-formyl-2,2':5',2"-terthiophene was dissolved in 20 ml of THF and stirred at room temperature, followed by adding 0.034 g of $NaBH_4$ and stirred for 2 hours. After the reduction was completed, 50 ml of water was added. The solution was then extracted with chloroform, dried over anhydrous $Na_2SO_4$, filtered and condensed. The yellowish powder was thus obtained and the melting point thereof was 151°–152° C. (yield was 97%).

Data of Spectra:

UVmax: 355 nm

IR (KBr): $cm^{-1}$ 3500–3076 —OH 3061 C=C—H, 2950 —CH$_2$— 1060 —C—O—

$^1$H-NMR (DMSO): δ value 4.60 (2H, d, —CH$_2$—, J=6) 5.52 (—OH J=6) 6.91 (1H, H$_{5''}$, d, J=4) 7.09 (1H, H$_{4''}$, dd, J=3.5, 4) 7.15 (1H, H$_{4' or 3'}$, d, J=4) 7.20 (1H, H$_{3' or 4'}$, d, J=4) 7.24 (1H, H$_4$, d, J=4.0) 7.31 (1H, H$_{3''}$, d, d, J=, 1, 4) 7.51 (1H, H$_3$, d, J=4)

Mass: m/e (relative intensity) 278 ($M^+$)

EXAMPLE 46

Synthesis of 5-carboxy-2,2':5',2"-terthiophene 0.27 g of 5-formyl-2,2':5',2"-terthiophene was dissolved in 50 ml of acetone and the temperature thereof was maintained at 15° C. $CrO_3/H_2O/H_2SO_4$ solution (0.9 g/12 ml/0.2 ml) was dropped in slowly and stirred for 4 hours at 40° C. Then 50 ml of water was dropped in slowly, and the solution was filtered, washed with water, dried and a yellowish solid was thus obtained. After washed with chloroform, 150 mg of product was obtained and the melting point thereof was 239°–240° C. (yield: 51%).

Data of Spectrum:

UVmax: 340 nm Peak 1 365 nm Peak 2

IR (KBr): $cm^{-1}$ 3200–2500 —OH 1664 C=O 1263 C—O 1435 —O—H $^1$H-NMR (DMSO): δ value 9.9 (1H, —COOH) 8.03 (s, 1H) 7.52–7.68 (6H)

Mass: m/e 292 ($M^+$)

EXAMPLE 47

Synthesis of 5-bromo-2,2':5',2"-terthiophene 4.96 g of 2,2':5',2"-terthiophene was dissolved in chloroform/acetic acid, followed by adding 3.7 g of NBS and stirred for 16 hours. After 200 ml of water was added, the reaction solution was extracted with chloroform, washed with $Na_2CO_3$ solution, dried over anhydrous magnesium sulfate, filtered, condensed and recrystallized with chloroform/n-hexane. The yellowish needle-like crystal was thus obtained and the melting point thereof was 137°–138° C. (yield was 82%).

EXAMPLE 48

Synthesis of 5-iodo-2,2':5',2"-terthiophene 2.33 g of 2,2':5',2"-terthiophene was dissolved in 70 ml of methanol. 25 ml of ethanol containing 1.10 g of $I_2$ was added, followed by dropping in 1 ml of water containing 0.47 g of $HIO_3$ slowly and the temperature thereof was maintained at 31° C. After the reaction solution was stirred for 4 hours, the color thereof changed from red to yellow and some precipitates generated. The precipitates were then dissolved in ethyl acetate and filtered. The filtered solution was evaporated under reduced pressure and recrystallized product (1.82 g) was thus obtained and the melting thereof was 146°–148° C. (yield was 97.3%).

EXAMPLE 49

Synthesis of 5-ethoxymethyl-2,2':5',2"-terthiophene (1) 5-Formyl-2,2':5',2"-terthiophene (0.3 g) was dissolved in ethanol (20 ml) by stirring at room temperature. To the solution, 0.04 g of $NaBH_4$ was slowly added. After the solution became clear in about 20 minutes, diluted hydrochloric acid was slowly added until bubbling stopped. The stirring was continued for about 12 hours, followed by chloroform extraction and silica gel column chromatography (eluted by ethyl acetate/n-hexane=1/19). The product was 5-ethyl-α-terthienylmethyl ether, which recrystallized with chloroform/ethyl acetate mixture to give a slightly yellowish platelet crystal (melting point 76°–77° C.). The yield was about 41%.

(2) The yield could be increased to 85% or higher by substituting absolute ethanol for alcohol and concentrated hydrochloric acid for diluted hydrochloric acid.

(3) 5-Hydroxymethyl-2,2':5',2"-terthiophene (0.2 g) was first dissolved in absolute ethanol (15 ml) at room temperature. To the solution, 0.03 ml of concentrated hydrochloric acid/absolute ethanol mixture (0.3 ml of concentrated HCl in 10 ml of absolute ethanol) was then added. After stirring for 2 hours, 0.8 g of sodium bicarbonate ($NaHCO_3$) was added and the stirring was continued for 0.5 hour followed by filtration. The ethanol was removed under reduced pressure. The yield of 5-ethoxymethyl-α-terthiophene thus obtained was also higher than 85%.

(4) 2.9 g of 5-formyl-2,2':5',2"-terthiophene was dissolved in absolute ethanol (75 ml). $NaBH_4$ (0.5 g) was added and stirred for 10 minutes. The solution was clear-yellow. 2.5 ml of phosphorusoxychloride added to an absolute ethanol was dropped into aforementioned mixture and stirred under the nitrogen atmosphere overnight. Then the solution was extracted with ethyl acetate. The extract was washed with water and dried over anhydrous magnesium sulfate. The solvent was removed under reduced pressure. The crude product was purified by column chromatography. The slightly yellowish crystal was obtained and the melting point thereof was 76°–77° C. The yield was 85%.

Data of spectra:

$^1$H-NMR ($CDCl_3$): δ value 7.20–6.87 (m, 7H, protons of thiophene) 4.62 (s, 2H, $—CH_2OC_2H_5$) 3.55 (q, 2H, $—CH_2OCH_2CH_3$) 1.25 (t, 3H, $—OCH_2CH_3$)

IR (KBr): $cm^{-1}$ 3050 (aromatic CH) 2971, 2852 (saturated CH) 1091 (—C—O—)

Mass: m/e (relative intensity) 306 ($M^+$, 100) 261 ($M^+$—$OC_2H_5$, 33)

EXAMPLE 50

Synthesis of 5-cyano-2,2':5',2"-terthiophene & 5,5"-dicyano-2,2':5',2"-terthiophene 0.52 g of 2,2':5',2"-terthiophene was dissolved in dichloromethane under nitrogen gas atmosphere and the temperature thereof was maintained at 0° C. To the mixture, chlorosulfonic isocyanate/$CH_2Cl_2$ (0.3 g/3 ml) solution was dropped into the mixture in 10 minutes. After the dropping was finished, the stirring was continued for 1 hour and DMF/$CH_2Cl_2$ (0.2 g/8 ml) was then dropped in to dissolve the yellow precipitate, followed by stirring for further 2 hours. $CH_2Cl_2$ was then added into the reaction mixture, dried over anhydrous magnesium sulfate and separated by silica gel chromatography. From the eluate of n-hexane, 0.063 g of α-T was recovered and from the eluate of ethyl acetate/n-hexane (3/197), 5-cyano-2,2':5',2"-terthiophene (0.2 g) was obtained and the melting point thereof was 117°–118° C. (yield was 41%). If the ratio of ethyl acetate/n-hexane shifted to (1/19), yellow powder of 5,5"-dicyano-2,2':5',2"-terthiophene (15 mg) was obtained and the melting point thereof was 208°–210° C. (yield was 3%).

Data of Spectra:

UVmax: 375 nm α-T-CN 380 nm NC-α-T-CN

IR (KBr): $cm^{-1}$ 2212.3 α-T-CN 22 14.3 NC-α-T-CN $^1$H-NMR ($CDCl_3$): δ value 5-cyano-2,2':5',2"-terthiophene 7.05 (dd, 1H, $J_{5-6,6-7}$=4, 5) 7.12 (d, 1H, J=4) 7.11 (d, 1H, J=4) 7.18 (d, 1H, J=4) 7.28 (dd, 1H, J=, 1, 5) 7.53 (d, 1H, J=4)

$^1$H-NMR ($CDCl_3$): δ value 5,5"-dicyano-2,2':5',2"-terthiophene 7.19 (d, 2H, J=4) 7.26 (s, 2H) 7.71 (d, 2H, J=4)

Mass: m/e (relative intensity) 273 ($M^+$) α-T-CN 298 ($M^+$) NC-α-T-CN

EXAMPLE 51

Synthesis of 5-(2-carboxy-1-ethenyl)-2,2'-bithiophene 3.88 g of 5-formyl-2,2'-bithiophene, 4.16 g of malonic acid, 15.5 ml of pyridine and 1.4 g of piperidine were heated and stirred at 90° C. in oil bath for 2 hours. Then raised the temperature to 120° C. for 10 minutes. The reaction mixture was cooled down to room temperature and diluted with 100 ml of distilled water. 40 ml of concentrated HCl was added to acidify the solution. The orange precipitate thus crystallized was further purified by silica gel chromatography. From the eluate of acetone/n-hexane (2/5), 2.95 g of product was thus obtained and the melting point thereof was 175° C. ($M^+$: 236). 0.16 g of pure 5-(2-dicarboxy-ethenyl)-2,2'-bithiophene was also obtained and the melting point thereof was 220°–221° C.

Data of Spectra:

Mass: m/e 280($M^+$) 236 ($M^+$—COOH)

EXAMPLE 52

Synthesis of 5-(2-ethoxycarbonyl-1-ethenyl)-2,2'-bithiophene 0.25 g of sodium metal was dissolved in 20 ml of absolute ethanol. 4 ml of ethyl acetate previously dried over 4A molecule sieve was stirred in ice bath and 1 g of 5-formyl-2,2'-bithiophene dissolved in 10 ml of ethyl acetate was then dropped in. The solution was heated to 50° C., stirred for 15–20 hours and solid sodium could be added if the reaction was incomplete. After the reaction was completed, 3 ml of acetic acid was added and the precipitate was dissolved immediately. The solution was further stirred for 30 minutes and 30 ml of water was then added for separating the ethyl acetate layer. The separated ethyl acetate layer was washed with water twice, dried over anhydrous magnesium sulfate, filtered and purified by silica gel chromatography. From the eluate of ethyl acetate/n-hexane (248/2) 1.11 g of yellowish needle-like product was obtained and the melting point thereof was 60°–61° C.

Data of Spectra:

$^1$H-NMR (d-acetone): δ value 1.27 (3H, t), 4.18 (2H, q), 6.17 (1H, d), 7.70 (1H, t), 7.21 (1H, d) 7.31 (1H, d), 7.33 (1H, d), 7.45 (1H, d), 7.72 (1H, d)

IR (KBr): $cm^{-1}$ 3060 aromatic C—H 3000, 2950 —$CH_2CH_3$ 1703 C=O 1614 —C=C—1208 —C—O—C—

Mass: m/e (relative intensity) 264 ($M^+$), 219 ($M^+$—OEt)

EXAMPLE 53

Synthesis of 5-(2,2-dicarboxyethenyl)-2,2'-bithiophene 3.9 g of 5-formyl-2,2'-bithiophene, 4.2 g of malonic acid, 10 ml of pyridine and 2.5 ml of piperidine were heated at 60° C. for 2 hours. After cooling, 50 ml of water was added into the mixture and acidified by diluted HCl. The crude product collected was recrystallized from ethanol to give a crystal product (5.65 g). The melting point of the product was 220°–221° C. The yield was 86%.

EXAMPLE 54

Synthesis of 5-(2,2-diethoxycarbonyl-ethenyl)-2,2,'-bithiophene 3.89 g of 5-formyl-2,2'-bithiophene, 3.50 g of diethylmalonate, 15 ml of pyridine and 2.4 ml of piperidine were heated at 80° C. for 3 hours. After cooling, the mixture was acidified by diluted HCl, extracted with ethyl acetate and purified by column chromatography. The orange crystal product (4.39 g) was obtained by recrystallization from ethanol. The melting point of the product was 60° C.

Data of Spectra:

$^1$H-NMR (d-acetone): δ value δ7.76 1H(s) —CH=C δ7.28–7.01 5H(m) protons of thiophene δ4.41 2H (q) $CH_3C\underline{H}_2O$—δ4.28 2H(q) $CH_3C\underline{H}_2O$—δ1.37 3H(t) $C\underline{H}_3CH_2O$—δ1.30 3H(q) $C\underline{H}_3CH_2O$—

IR (KBr): $cm^{-1}$ 1734, 1687 C=O 1606, 842, 790, 729 bithiophene

Mass: m/e (relative intensity) 336 ($M^+$)

EXAMPLE 55

Synthesis of 5-(2-ethoxycarbonyl-2-cyanoethenyl)-2,2'-bithiophene 3.9 g of 5-formyl-2,2'-bithiophene, 2.4 ml of cyano-ethylacetate, 15 ml of pyridine and 2.4 ml of piperidine were heated at 80°–85° C. for 2 hours. After cooling, the mixture was acidified by diluted HCl and then filtered. The orange crude product was recrystallized from ethanol to give a crystal product (5.02 g). The melting point of the product was 131° C. The yield was 86%.

Data of spectra:

IR (KBr): $cm^{-1}$ 2218, 1687 (—CN) 1699, 1687 (C=O) 1630, 839, 796, 729 (protons of bithiophene)

Mass: m/e (relative intensity) 289($M^+$)

EXAMPLE 56

Synthesis of 5-(3-carboxy-3-oxo-1-propenyl)-2,2'-bithiophene 5 g of 5-formyl-2,2'-bithiophene was dissolved in 70 ml of ethanol, followed by dropping in 5 ml of water containing 3.4 g of pyruvic acid sodium salt and stirring for 10 minutes. 1 ml of 50% NaOH solution was dropped into the solution and stirred for 3 hours. The precipitated solid was filtered and washed with ether. The solid was added in diluted HCl and extracted with ethyl acetate. 5.3 g of dark red crude product was obtained after column chromatography separation. The melting point of the product was 136°–142° C. The yield was 78%.

Data of Spectra:

$^1$H-NMR (400 MHz, $CDCl_3$+DMSO): δ value 7.84–7.88 (d, 1H, —CH=CH—) 6.91–7.28 (m, 6H, —CH=CH, protons of thiophene)

IR (KBr): $cm^{-1}$ 3500–2500 (carboxy OH), 1720, 1670, 1580 (conjugative unsaturated bond C=O), 1450

Mass (75ev): m/e (relative intensity) 264 ($M^+$, 37), 219 (100)

EXAMPLE 57

Synthesis of 5-(3-methoxycarbonyl-3-oxo-1-propenyl)-2,2,'-bithiophene 5-(3-Carboxy-3-oxo-1-propenyl)-2,2'-bithiophene (0.62 g) was dissolved in a mixture of ethanol (25 ml) and benzene (15 ml). Little p-toluenesulfonic acid was added and refluxed for 6 hours. The solution was monitored by thin layer chromatography to determine whether the reaction was completed. Then the solution was extracted with ethyl acetate, washed with water and aqueous $NaHCO_3$ solution. After evaporation of solvent, the crude product was purified by column chromatography. From the eluate of ethyl acetate/n-hexane (1/9), slightly yellowish crystal (0.63 g) was obtained and the melting point thereof was 78° C. The yield was 97%

Data of spectra:

$^1$H-NMR 400 MHz ($CDCl_3$): δ value 7.90–7.94 (d, 1H, —CH=CH—) 6.91–7.31 (m, 6H, —CH=CH—, protons of thiophene) 3.89 (s, 3H, —$COOCH_3$)

IR (KBr): $cm^{-1}$ 1730, 1690 (C=O), 1650, 1600, 1580 (conjugative unsaturated bond), 1440, 1270, 1080

Mass spectrum (75 ev), m/e (relative intensity) 278($M^+$, 16), 265(100), 219(93)

EXAMPLE 58

Synthesis of 5-(2,2-dicarboxyethenyl)-2,2':5',2"-terthiophene 1.30 g of 5-formyl-2,2':5',2"-terthiophene, 1.04 g of malonic acid, 20 ml of pyridine and 0.1 ml of piperidine were heated at 50°–60° C. for 2 hours. 100 ml of water was added after reaction was completed. The mixture was acidified by diluted HCl and the precipitate collected was recrystallized from ethanol to give reddish crystal (1.43 g). The melting point thereof was 202°–203° C. The yield was 84%.

EXAMPLE 59

Synthesis of 5-hydroxyiminomethylidene-2,2'-bithiophene

To 1 g of hydroxylamine hydrochloride in 10 ml of ice water solution, 10 ml of 10% aqueous KOH was dropped in slowly. Then 50 ml of ethanol containing 3 g of 5-formyl-2,2'-bithiophene was dropped in and stirred for 1 hour. After the solution was heated to 50° C. and stirred for 3 hours, two kinds of product were generated (Rf=0.55, 0.6 developed by ethyl acetate/n-hexane (3/7)). The crude product was further separated by silica gel chromatography and the eluant was ethyl acetate/n-hexane (1/4). syn-5-hydroxyiminomethylidene-2,2'-bithiophene and anti-5-hydroxyiminomethylidene-2,2'-bithiophene were obtained and the melting point thereof was respectively 131° C. and 148° C.

Data of Spectra:

$^1$H-NMR (400 MHz, $CDCl_3$): δ value 8.21 (s, 1H, —OH) 7.20 (s, 1H, —CH=N—H—) 7.24–6.99 (m, 5H, protons of thiophene)

IR (KBr): $cm^{-1}$ 3300 (—OH), 1430, 1230, 1050, 960

Mass (75 ev): m/e (relative intensity) 209 ($M^+$, 100), 192 (25), 166 (41), 121 (50)

EXAMPLE 60

Synthesis of 5-hydrazonomethylidene-2,2'-bithiophene 3 g of 5-formyl-2,2'-bithiophene was dissolved in 50 ml of ethanol and 3 ml of hydrazine was dropped in slowly. 5 ml of $H_2SO_{4(aq)}$(2N) was then dropped into the reaction solution and stirred for 1 hour. It was monitored by thin layer chromatography to determine whether the reaction was completed. Two kinds of product were generated. Ethanol was removed under reduced pressure. Then, the crude product was extracted with ethyl acetate and washed with water. The solid obtained on removal of ethyl acetate was separated by column chromatography. The eluant was ethyl acetate/n-hexane (1/1). The mixture of syn-5-hydrazonomethylidene-2,2'-bithiophene and anti-5-hydrazonomethylidene-2,2,'-bithiophene were obtained and the melting point thereof was 202°–204° C.

Data of Spectra:

$^1$H-NMR (400 MHz, CDCl$_3$): δ value 8.68 (s, 1H, —CH=N—) 7.02–7.34 (m, 5H, protons of thiophene)

IR (KBr): cm$^{-1}$ 1610 (C=N), 1450, 1230, 1060, 930, 800, 690

EXAMPLE 61

Synthesis of 5-phenylhydrazonomethylidene-2,2'-bithiophene 0.5 g of 5-formyl-2,2'-bithiophene was dissolved in 100 ml of ethanol and 1 ml of phenylhydrazine was dropped in slowly. After the mixture was stirred for 10 minutes, 5 ml of HCl(2N) was dropped in and further stirred for 2 hours. It was monitored by thin layer chromatography to determine whether the reaction was completed. Ethanol was evaporated under reduced pressure. Then, ethyl acetate and water were added for extraction and the extracted crude product was separated by column chromatography. The eluant was ethyl acetate/n-hexane (1/9). The mixture of syn-5-phenylhydrazonomethylidene-2,2'-bithiophene and anti-5-phenylhydrazonomethylidene-2,2'-bithiophene were obtained and the melting point thereof was 128° C.

Data of Spectra:

$^1$H-NMR (400 MHz, CDCl$_3$): δ value 7.77 (s, 1H, —CH=N—) 6.82–7.56 (m, 5H, aromatic H)

IR (KBr): cm$^{-1}$ 3250 (N—H), 1660(C=N), 1600, 1260, 1120, 800

Mass (75 ev): m/e (relative intensity) 284 (M$^+$, 100), 166 (30), 121 (30), 91 (32)

EXAMPLE 62

Synthesis of 5-hydroxyiminomethylidene-2,2':5',2"terthiophene 0.5 g of 5-formyl-2,2':5',2"-terthiophene was dissolved in 150 ml of ethanol. 1.5 ml of water containing 0.85 g of hydroxylamine hydrochloride and 0.85 g of KOH was dropped in slowly. After the mixture was refluxed for 3 hours, the reaction mixture was cooled down and extracted with ethyl acetate. Ethyl acetate layer was washed with water and evaporated under reduced pressure. The crude product was further separated by column chromatography. The eluant was ethyl acetate/n-hexane (1/9). The mixture of syn-5-hydroxyiminomethylidene-2,2':5',2"-terthiophene and anti-5-hydroxyiminomethylidene-2,2':5',2"-terthiophene were thus obtained and the melting point thereof was respectively 165° C. and 190° C.

Data of Spectra:

$^1$H-NMR (400 MHz, CDCl$_3$): δ value 8.61 (s, 1H, —OH) 8.07 (s, 1H, —CH=N—) 7.05–7.37 (m, 7H, protons of thiophene)

IR (KBr): cm$^{-1}$ 1590 (—C=N—), 1450, 1230, 1060

EXAMPLE 63

Synthesis of 5-hydrazonomethylidene-2,2':5',2"-terthiophene 0.5 g of 5-formyl-2,2':5',2"-terthiophene was dissolved in 200 ml of ethanol. 2 ml of hydrazine was dropped in slowly. After 2 ml of H$_2$SO$_4$ (2N) was dropped in and stirred for 3 hours at room temperature, the reaction solution was monitored by thin layer chromatography to determine whether the reaction was completed. Ethanol was removed under reduced pressure. Then, it was extracted with ethyl acetate and treated in situ on column chromatographic separation. From the eluate of ethyl acetate/n-hexane (1/9) the mixture of syn-5-hydrazonomethylidene-2,2,:5,2"-terthiophene and anti-5-hydrazonomethylidene-2,2':5',2"-terthiophene were thus obtained.

EXAMPLE 64

Synthesis of 5-phenylhydrazonomethylidene-2,2':5',2"-terthiophene 1.5 g of 5-formyl-2,2':5,2"-terthiophene was dissolved in 200 ml of ethanol. 3 ml of phenyl-hydrazine and 10 ml of HCl (2N) were dropped in and stirred for 3 hours at room temperature. The reaction solution was monitored by thin layer chromatography to determine whether the reaction was completed. Ethanol was removed under reduced pressure. Then, extracted with ethyl acetate and treated in situ. The crude product was separated by column chromatography, and orange solid product was thus obtained. The melting point of the product was 197° C.

Data of Spectra:

$^1$H-NMR (400 MHz, CDCl$_3$+DMSO): δ value 7.67 (S, 1H, —C$\underline{H}$=N) 6.53–7.09 (m, 12H, aromatic H)

IR (KBr): cm$^{-1}$ 610 (C=N), 1485, 1260, 1060, 790, 750, 690

Mass (75 ev): m/e (relative intensity) 366 (M$^+$, 8), 210 (50), 150 (45), 108S (90), 102 (55), 77(100)

EXAMPLE 65

Synthesis of 5-3-hydroxy-1-propynyl)-2,2'-bithiophene

To the mixture of 48 mg (0.86 mmole) of propargyl alcohol, 1 ml of benzene, 0.1 g of 5-iodo-2,2'-bithiophene (0.34 mmole) was added 0.25 g of CuI, 0.05 g of benzyltriethylammonium chloride and 0.1 g of Pd(PPh$_3$)$_4$. To the solution, 3 ml of NaOH solution (2.5N) was added at room temperature and stirred for 2 hours. 4 ml of NH$_4$Cl solution was then added. The reaction solution was extracted with 50 ml of ethyl acetate. The extract was washed with 10 ml of HCl (10%) for 3 times, 50 ml of water twice and dried over anhydrous magnesium sulfate. The residual solid was purified by silica gel column chromatography. From the eluate of ethyl acetate/n-hexane (3/1) 56 mg of product (74%) was obtained.

Data of Spectra:

$^1$H-NMR 400 MHz (CDCl$_3$): δ value 2.3 (b, 1H, —OH) 4.5 (s, 2H, —CH$_2$) 6.9–7.3 (m, 5H, protons of thiophene)

$^{13}$C-NMR (CDCl$_3$): δ value 51.50, 78.89, 92.19, 121.11, 123.48, 128.06, 133.4, 136.70, 139.25

IR (neat): cm$^{-1}$ 3350 (OH), 2250 (C≡C)

EXAMPLE 66

Synthesis of 5-(3-acetoxy-1-propynyl)-2,2'-bithiophene 0.8 g (3.64 mmole) of 5-(3-hydroxy-propynyl)-2,2'-bithiophene was dissolved in a mixture of 0.5 ml of acetic anhydride and 1.5 ml of pyridine at room temperature and stirred for 2 hours. The reaction solution was extracted with ethyl acetate. The extract was washed with 10 ml of HCl (10%) for 3 times, 10 ml of NaOH solution for 3 times, 50 ml of water twice and dried over anhydrous magnesium sulfate. The residual solid was further purified by silica gel column chromatography. The eluant was ethyl acetate/n-hexane (1/10). 0.71 g of slightly brownish-yellow oily product (73%) was obtained.

Data of Spectra:
$^1$H-NMR (CDCl$_3$): δ value 2.11 (s, 3H, —CH$_3$) 4.90 (s, 2H, —CH$_3$) 6.97–7.22 (m, 5H, protons of thiophene)
IR (neat): cm$^{-1}$ 2250 (C≡C), 1745 (C=O), 1225
Mass: m/e (relative intensity) 262 (M$^+$, 100) 202 (65)

EXAMPLE 67

Synthesis of 5-(3-hydroxy-1-butynyl)-2,2'-bithiophene

To the mixture of 1 g (14.3 mmole) of 3-hydroxy-1-butyne, 10 ml of benzene and 2.78 g of 5-iodo-2,2'-bithiophene (9.52 mmole) was added 0.15 g of CuI, 0.15 g of benzyltriethylammonium chloride, 0.2 g of Pd(PPh$_3$)$_4$ and then 15 ml of NaOH solution (2.5N) at room temperature and stirred for 2 hours. 4 ml of NH$_4$Cl solution was then added. The reaction solution was extracted with ethyl acetate. The extract was washed with 10 ml of HCl (10%) for 3 times, 50 ml of water twice, and dried over anhydrous magnesium sulfate. The crude product was purified by silica gel column chromatography. From the eluate of ethyl acetate/n-hexane (3/1) 2.07 g of yellow solid product (93%) was obtained.

Data of Spectra:
IR (KBr): cm$^{-1}$ 3450 (OH), 810
$^1$H-NMR (CDCl$_3$): δ value 1.55 (d, 3H, OH) 2.85–3.05 (b, 1H, OH) 4.70–4.91 (q, 1H, CH) 6.95–7.20 (m, 5H, protons of thiophene)
Mass: m/e (relative intensity) 234 (M$^+$,100), 219 (58)

EXAMPLE 68

Synthesis of 5-(2-ethoxycarbonyl-ethynyl)-2,2'-bithiophene

To the mixture of 1 g (10.2 mmole) of ethyl propiolate, 5 ml of benzene, 19.8 g of 5-iodo-2,2'-bithiophene (6.87 mmole) was added 0.1 g of CuI, 0.1 g of benzyltriethylammonium chloride, 0.2 g of Pd(PPh$_3$)$_4$ and 15 ml of NaOH solution (2.5N) at room temperature and stirred for 4 hours. 10 ml of NH$_4$Cl solution was then added. The reaction solution was extracted with ethyl acetate. Then, the extract was washed with 10 ml of HCl (10%) for 3 times, 50 ml of water twice and dried over anhydrous magnesium sulfate. The residual solid obtained from the evaporation of ethyl acetate was purified by silica gel column chromatography. From the eluate of ethyl acetate/n-hexane (10/1) 0.31 g of yellow solid product (17.5%) was thus obtained.

Data of Spectra:
$^1$H-NMR (CDCl$_3$): δ value 1.35 (t, 3H, CH$_3$) 4.31 (q, 2H, CH$_2$) 7.01–7.41 (m, 5H, protons of thiophene)
IR (KBr): cm$^{-1}$ 2250 (C≡C), 1710 (C=O)
Mass: m/e (relative intensity) 262 (M$^+$, 100), 190 (73)

EXAMPLE 69

Synthesis of 5-(3-oxo-1-butynyl)-2,2,'-bithiophene

To the mixture of 1 g (14.7 mmole) of 1-butynyl-3-one, 5 ml of benzene, 2.86 g of 5-iodo-2,2'-bithiophene (9.79 mmole) was then added 0.1 g of CuI, 0.1 g of benzyltriethylammonium chloride, Pd(PPh$_3$)4 (0.2 g) and 5 ml of NaOH solution (2.5N) at room temperature and stirred for 5 hours. 10 ml of NH4Cl solution was then added. The reaction solution was extracted with ethyl acetate. Then, the extract was washed with 10 ml of HCl (10%) for 3 times, 50 ml of water twice, condensed and dried over anhydrous magnesium sulfate. 0.81 g of orange solid product (36%) was thus obtained.

Data of Spectra:
$^1$H-NMR (CDCl$_3$): δ value 2.47 (s, 3H, CH3) 7.01–7.42 (m, 5H, protons of thiophene)
IR (KBr): cm$^{-1}$ 2200 (C≡C), 1660 (C=O)
Mass: m/e (relative intensity) 232 (M$^+$, 100), 217 (64)

EXAMPLE 70

Synthesis of 5-(2-ethoxycarbonyl-ethynyl)-2,2,:5',2"-terthiophene

To the mixture of 78 mg (0.8 mmole) of ethyl propiolate, 3 ml of benzene, 0 2 g of 5-iodo-2,2':5',2"-terthiophene (0.53 mmole) was added 0.05 g of CuI, 0.05 g of benzyltriethylammonium chloride, 0.1 g of Pd(PPh$_3$)$_4$ and 5 ml of NaOH solution (2.5N). The temperature of the mixture was then raised to 40° C. and stirred for further 5 hours. 5 ml of NH$_4$Cl solution was added. The reaction solution was extracted with ethyl acetate. The extract was washed with 10 ml of HCl (10%) for 3 times, 50 ml of water twice and dried over anhydrous magnesium sulfate. The crude product was purified by silica gel column chromatography. From the eluate of ethyl acetate/n-hexane (1/15), 78 mg of slightly brown product (42%) was obtained and the melting point thereof was 93° C.

Data of Spectra:
$^1$H-NMR (CDCl$_3$): δ value 1.35 (t, 3H, —CH$_3$) 4.31 (q, 2H, —CH$_3$) 6.90–7.41 (m, 5H, protons of thiophene)
IR (KBr): cm$^{-1}$ 2200 (C≡C), 1705 (C=O)
Mass: m/e (relative intensity) 344 (M$^+$, 17), 248(100)

EXAMPLE 71

Synthesis of 5-(2-carboxy-ethenyl)-2,2':5',2"-terthiophene 276 mg of 5-formyl-2,2'-terthiophene, 0.212 g of malonic acid, 10 ml of pyridine and 1 ml of piperidine were heated in water bath for 2 hours and then refluxed for 30 minutes. After cooled down the reaction solution was then poured into water. The mixture was acidified by diluted HCl. After kept 3 hours at room temperature and then filtered. The reddish-brown solid was washed with water and recrystallized from ethanol to give copper red needle-like crystal and the melting point of the product was 237°–238° C.

The yield was 78.6%.

Data of Spectra:
UV: 395 nm
IR (KBr): cm$^{-1}$ 3200–2300 OH 1672 C=O 1616 —CH=CH—1220 —C—C—1425 —OH
$^1$H-NMR (d$_6$—DMSO): δ value 6.13 (1H, —CH=CH—COOH, d, J=16) 7.1 (1H, H4", t. J=4) 7.3 (1H, H4, d. J=4) 7.37 (3H, H3'4'3", m) 7.48 (1H, H5", d. J=4) 7.56 (1H, H3, d. J=5) 7.70 (1H, —CH=CH—COOH, d, J=16)
Mass: m/e (relative intensity) 318 (M$^+$)

EXAMPLE 72

Synthesis of 5-(3-carboxy-3-oxo-1-propenyl)-2,2':5',2"-terthiophene 0.5 g of 5-formyl-2,2':5',2"-terthiophene was dissolved in 40 ml of ethanol, followed by dropping in 3 ml of water containing 0.3 g of pyruvic acid salt and stirring for 10 minutes. 1 ml of 50% NaOH solution was dropped into the solution and stirred overnight. The reaction solution was acidified by diluted HCl and extracted with 100 ml of ethyl acetate. The extract was treated in situ and separated by column chromatography. Unreactive materials were eluted by ethyl acetate/n-hexane (1/9). The black solid product was eluted by ethyl acetate.

EXAMPLE 73

Synthesis of 5-(3-methoxycarbonyl-3-oxo-1-propenyl)2,2':5',2''-terthiophene 0.2 g of 5-(3-carboxy-3-oxo-1-propenyl)-2,2':5',2''-terthiophene was dissolved in 20 ml of methanol. Little p-toluenesulfonic acid was added and refluxed overnight. Then the methanol was evaporated under reduced pressure and the crude product was purified by column chromatography. From the eluate of ethyl acetate/n-hexane (1/9). The dark reddish crystal product was obtained.

Data of Spectra:
$^1$H-NMR (400 MHz, CDCl$_3$): δ value 7.9–7.94 (d, 1H, —CH═CH—) 7.01–7.32 (m, 6H, —CH═CH—, protons of thiophene) 3.91 (s, 3 h, —COOCH$_3$)

Mass spectrum (75 ev): m/e (relative intensity) 360 (M$^+$, 53), 301 (100), 282 (23)

EXAMPLE 74

Synthesis of 2,2':5',2'':5'',2'''-tetrathiophene 10 ml of (34.2 mmole) 5-iodo-2,2'-bithiophene and 2.8 g of Cu powder (44 mmole) were added into 20 ml of DMF. After refluxed for 6 hours, the reaction mixture was extracted with THF and filtered. Crude solid was obtained by addition of excess water. The crude product was purified by silica gel column chromatography. From the eluate of n-hexane, unreactive materials was recovered, followed by elution with n-hexane/tetrahydrofuran (2/1). 2 g of dark yellow crystal (34.8%) was obtained. The melting point of the product was 208° C.

EXAMPLE 75

Synthesis of 5-formyl-2,2':5',2'':5'',2'''-tetrathiophene 10 ml of dimethyl formamide (30 ml) was stirred and cooled in ice bath for 10 minutes. 0.2 ml of POCl$_3$ (1.94 mmole) was added into the solution at 0° C. and stirred for 1 hour. 20 ml of dimethyl formamide solution of tetrathiophene (0.5 g, 1.49 mmole) was dropped in slowly. The mixture was stirred for 1 hour at 0° C., then the temperature was raised to room temperature and further stirred for 8 hours at 70° C. The reaction solution was cooled and poured into NaOH ice water solution. Then, the solution was extracted with dichloromethane, washed with 50 ml of water for 3 times, dried over anhydrous magnesium sulfate and condensed. The crude product was further purified by silica gel column chromatography. The eluant was n-hexane/tetrahydrofuran (1/1). 0.22 g of dark yellow solid (41%) product was obtained after recrystallized by the mixture of n-hexane and tetrahydrofuran. The melting point of the product was 215° C.

Data of Spectra:
$^1$H-NMR (CDCl$_3$): δ value 7.00–7.66 (m, 9H, protons of thiophene) 9.84 (s, 1H, —CHO)
IR (KBr): cm$^{-1}$ 1665 (C═O)
Mass: m/e (relative intensity) 358 (M$^+$, 100)

EXAMPLE 76

Synthesis of 5-hydroxymethyl-2,2':5',2'':5'',2'''-tetrathiophene 180 mg of 5-formyl-2,2':5',2'':5'',2'''-tetrathiophene (0.51 mmole) was dissolved in 10 ml of tetrahydrofuran. 0.1 g of NaBH$_4$ was then added. The mixture was stirred for 2 hours at room temperature. Then the solution was extracted with dichloromethane and washed with 10 ml of water twice and condensed to give crude product. The crude product was purified by silica gel column chromatography and further recrystallized with THF and n-hexane. 150 mg of orange-yellow solid (82.4%) was obtained and the melting point of the product was 216° C.

Data of Spectra:
IR (KBr): cm$^{-1}$ 2300 (OH)
Mass: m/e (relative intensity) 360 (M$^+$, 100) 344 (21)

EXAMPLE 77

Synthesis of 5-(4-hydroxy-1-butynyl)-2,2'-bithiophene (1) To the mixture of 0.23 g (3.28 mmole) of 4-hydroxy-1-butyne, 1 ml of benzene, 0.3 g of 5-iodo-2,2''-bithiophene (1.03 mmole) was added 0.05 g of CuI, 0.05 g of benzyltriethylammonium chloride, 0.1 g of Pd(PPh$_3$)$_4$ and 4 ml of NaOH solution (2.5N) at room temperature and stirred for 2 hours. 5 ml of NH$_4$Cl solution was then added. The reaction solution was extracted with ethyl acetate. The extract was then washed with 10 ml of HCl (10%) for 3 times, 50 ml of water twice and dried over anhydrous magnesium sulfate. The residual solid was purified by silica gel column chromatography. From the eluate of ethyl acetate/n-hexane (1/3) 0.21 g of slightly yellowish product (75%) was obtained and the melting point thereof was 67° C.

(2) 17.07 g of 5-iodo-2,2'-bithiophene was dissolved in 100 ml of pyridine. Cuprous salt of 3-butyne-1-ol were added into the solution and refluxed for 3 hours under nitrogen gas atmosphere. After the reaction was completed, pyridine was evaporated under reduced pressure. The reside was then extracted with dichloromethane two times (100 ml ×2) and filtered to eliminate the particles. The extract was washed with water (150 ml ×2), 10% NaHCO$_3$ solution (100 ml ×2) and water (150 ml ×2) again to remove the water soluble materials. The organic layer was dried over anhydrous magnesium sulfate, filtered and the solvent was recovered. The crude product was separated by silica gel chromatography. From the eluate of n-hexane, 3.56 g of 2,2'-bithienyl was recovered, and from the eluate of ethyl acetate/n-hexane (1/6), 8.49 g of yellowish crystal product (62%) was obtained.

Data of Spectra:
$^1$H-NMR: δ value 6.75–7.20 (m, 5H, protons of bithiophene) 3.7 (t, 2H, —CH$_2$OH) 2.7 (t, 2H, —CH$_2$CH$_2$OH)
IR: cm$^{-1}$ 3300 (broad) OH 1032 C—O 835, 830, 795, 705, 690 2,2'-bithiophene
Mass: m/e (relative intensity) 234 (M$^+$, 17) 203 (M$^+$—CH$_2$OH, 10) 84 (thiophene, 100)

EXAMPLE 78

Synthesis of 5-(4-tosyloxy-1-butynyl)-2,2'-bithiophene 8.48 g of 5-(4-hydroxy-1-butynyl)-2,2'-bithiophene was dissolved in 100 ml of pyridine. 16 g of p-tosyl chloride was added in under nitrogen gas atmosphere. After stirred overnight, the pyridine was evaporated under reduced pressure. The reside was extracted with ethyl acetate (100 ml) twice, filtered, washed with water (100 ml) twice, HCl solution twice (5%, 100 ml) and water (100 ml) twice again. The organic layer dried over anhydrous magnesium sulfate was filtered and the solvent thereof was evaporated. The residual solid was further purified by rapid silica gel column chromatography. From the eluate of ethyl acetate/n-hexane (1/6). 6.25 g of 5-(4-tosyloxy-1-butynyl)-2,2,'-bithiophene and 1.48 g of 5-(4-chloro-1-butynyl)-2,2'-bithiophene were respectively obtained and the yield thereof was 44% and 16%.

Data of Spectra:
$^1$H-NMR: δ value 6.8–7.8 (m, 9H, aromatic) 4.06 (t, 2H, —CH$_2$CH$_2$—O—) 2.75 (t, 2H, —CH$_2$CH$_2$—O—) 2.33 (s, 3H, —CH$_3$)

IR: cm$^{-1}$ 3030 (aromatic C—H) 2950, 2910 (aliphatic C—H) 1340, 1170 (—SO$_2$—) 970 (S—O) 885, 800, 755, 690, 66, 2,2'-bithiophene Mass: m/e (relative intensity) 388 (M$^+$, 82) 216 (M$^+$—Tosyl—H, 100)

EXAMPLE 79

Synthesis of 5-(4-chloro-1-butynyl)-2,2'-bithiophene 2.34 g of 5-(4-hydroxy-1-butynyl)-2,2'-bithiophene was dissolved in 50 ml of pyridine. 2.0 g of POCl$_3$ was added in under nitrogen gas atmosphere. After stirred for 4 hours, the pyridine was evaporated. The reside was extracted with ethyl acetate (50 ml ×2) and the extract was washed with saturated NaCl solution twice (100 ml) and water (50 ml) twice. The organic layer was then separated and dried over anhydrous magnesium sulfate. After the organic layer was filtered and the solvent thereof was removed under reduced pressure, the residual solid was further purified by rapid silica gel column chromatography and from the eluate of ethyl acetate/n-hexane (1/5), 1.80 g of product was thus obtained and the yield thereof was 71%.

Data of Spectra:
$^1$H-NMR: δ value 6.9–7.3 (m, 5H, protons of bithiophene) 3.65 (t, 2H, —CH$_2$—CH$_2$—Cl) 2.90 (t, 2H, —CH$_2$—CH$_2$—Cl)

IR: cm$^{-1}$ 3050, 3030 (aromatic C—H) 2960, 2910 (aliphatic C—H) 2205 (—C≡C—) 835, 790, 740, 685, 658 (2,2'-bithiophene)

Mass: m/e (relative intensity) 252 (M$^+$, 100) 216 (M$^+$—Cl, 4) 203 (M$^+$—CH$_2$Cl, 23)

EXAMPLE 80

Synthesis of 5-(but-3-en-1-ynyl)-2,2'-bithiophene (1) synthesis from tosylate ester 6.26 g of 5-(4-tosyloxy-1-butynyl)-2,2'-bithiophene was dissolved in 60 ml of ethanol. Aqueous ethanol containing 10 g of NaOH (ethanol: water=1:1) was dropped in 10 minutes and stirred at 75° C. for 15 minutes. The ethanol in the reaction mixture was then removed under reduced pressure, extracted with ethyl acetate (50 ml) twice and washed with saturated NaCl solution twice (50 ml) and water (50 ml) twice. The organic layer was then separated and dried over anhydrous magnesium sulfate. The solvent thereof was removed under reduced pressure after filtration, the residual solid was further purified by silica gel column chromatography and from the eluate of ethyl acetate/n-hexane (1/1), 2.83 g of product was thus obtained and the yield thereof was 81%.

Data of Spectra:
$^1$H-NMR: δ value 6.90–δ7.25 (m, 5H, protons of bithiophene) 5.14–6.2 (m, 3H, —CH=CH$_2$)

IR: cm$^{-1}$ 3100, 3050 (aromatic —C—H—) 2195 (—C≡C—) 1600, 1500 (aromatic —C=C—) 960, 910 (—CH=CH$_2$) 835, 790, 680 (2,2'-bithiophene)

Mass: m/e (relative intensity) 216 (M$^+$, 100)

(2) synthesis from chloride compound 5-(4-chloro-1-butynyl)-2,2'-bithiophene was dissolved in ethanol. KOH dissolved in ethanol was then added in and heated at 75° C. for 15 minutes. The remaining process was as described in procedure(a) and the same product was obtained. The yield was above 90%.

EXAMPLE 81

Synthesis of 5-(4-acetoxy-1-butynyl)-2,2'-bithiophene 1.23 g of 5-(4-hydroxy-1-butynyl)-2,2'-bithiophene was dissolved in 6 ml of pyridine. 1 ml of acetic anhydride was added at room temperature. After the reaction mixture was stirred for few minutes and further kept overnight. 20 ml of water was added and the oily layer was extracted with 30 ml of ethyl acetate. The extract was washed with HCl solution (10 ml, 1N) for 3 times, water (10 ml) once and diluted KHCO$_3$ solution (10 ml) once. Ethyl acetate was then removed under reduced pressure. The residual solid was purified by silica gel column chromatography. From the eluate of ethyl acetate/n-hexane (1/19) 1.7 g of slightly yellowish oily product was obtained after removal of the solvent.

Data of Spectra:
$^1$H-NMR: δ value 7.3–6.8 (m, 5H, protons of bithiophene) 4.16 (t, 2H, —CH$_2$—CH$_2$—O—) 2.7 (t, 2H, —CH$_2$—CH$_2$—O—) 2.0 (t, 3H, —OCOCH$_3$)

IR: cm$^{-1}$ 3035 (aromatic C—H) 2960, 2900 (aliphatic C—H) 1737, 1232, 1038 (ester) 830, 795, 692 (2,2'-bithiophene)

Mass: m/e (relative intensity) 276 (M$^+$, 46) 216 (M$^+$—AcOH, 100)

EXAMPLE 82

Synthesis of 5-(4-isovaleryloxy-1-butynyl)-2,2,'-bithiophene 1 g of 5-(4-hydroxy-1-butynyl)-2,2'-bithiophene was dissolved in 10 ml of pyridine. 1 ml of isovaleroyl chloride was added at room temperature, stirred for few minutes and kept overnight. The reaction mixture was treated as in acetate example 81. 1.06 g of slightly yellowish oily product was then obtained.

Data of Spectra:
$^1$H-NMR: δ value 6.95–7.1 (m, 5H, protons of bithiophene) 4.2 (t, 2H, J=7 Hz, —CH$_2$—CH$_2$—O—) 2.72 (t, 2H, J=7 Hz, —CH$_2$—CH$_2$—O—) 2.18 (br.s. 2H, —O—CO—CH$_2$—) 2.2–1.9 (m, 1H, —CH$_2$—CH(CH$_3$)$_2$) 0.96 (1, 6H, J=6 Hz, CH(CH$_3$)$_2$)

IR: cm$^{-1}$ 3100, 3070 (aromatic C—H) 2960–2870 (aliphatic C—H) 1730, 1250, 1150 (ester) 1460, 1380, 1360 (—CH(CH$_3$)$_2$) 834, 795, 692 (2,2'-bithiophene)

Mass: m/e (relative intensity) 318 (M$^+$, 15) 216 (M$^+$—(CH$_3$)$_2$CHCH$_2$COOH, 100)

EXAMPLE 83

Synthesis of 5-(4-benzoxy-1-butynyl)-2,2'-bithiophene 0.8 g of 5-(4-hydroxy-1-butynyl)-2,2'-bithiophene was dissolved in 8 ml of pyridine. 1 ml of benzoyl chloride was added at room temperature, stirred for few minutes and kept overnight. The reaction mixture was treated as in acetate example 81. Slightly yellowish crystal was then obtained and the melting point thereof was 61° C.

Data of Spectra:
$^1$H-NMR: δ value 6.86–8.28 (m, 10H, aromatic H) 4.42 (t, 2H, —CH$_2$—CH$_2$—O—) 2.85 (t, 2H, —CH$_2$—CH$_2$—O—)

IR: cm$^{-1}$ 3090, 3040 (aromatic C—H) 1695, 1268, 1109 (aromatic ester) 830, 800, 700 (2,2'-bithiophene)

Mass: m/e (relative intensity) 388 (M$^+$, 16) 16 (M$^+$—C$_6$H$_5$COOH, 100)

EXAMPLE 84

Synthesis of 5-(4,-palmityloxy-1-butynyl)-2,2'-bithiophene 0.6 g of 5-(4-hydroxy-1-butynyl)-2,2'-bithiophene was dissolved in 10 ml of pyridine. 1 ml of palmitoyl chloride was added at room temperature, stirred for few minutes and kept overnight. The reaction mixture was treated as in acetate example 81. 1.2 g of slightly yellowish crystal was thus obtained and the melting point thereof was 68°–69° C.

Data of Spectra:

$^1$H-NMR: δ value 7.26–6.84 (m, 5H, protons of thiophene) 4.25 (t, 2H, —CH$_2$—C$\underline{H}_2$—O—) 2.67 (t, 2H, —C$\underline{H}_2$—CH$_2$—O—) 2.28 (t, 2H, —OCOC$\underline{H}_2$C$_{14}$C$_{29}$) 1.22 broad (m, 29H, —OCOCH$_2$C$_{14}\underline{H}_{29}$)

IR: cm$^{-1}$ 3030 (aromatic C—H) 950, 2840 (aliphatic C—H) 730, 1170 (ester) 30, 795, 670 (2,2'-bithiophene)

Mass: m/e (relative intensity) 472 (M$^+$, 25) 16 (M$^+$—C$_{15}$H$_{31}$COOH, 100)

EXAMPLE 85

Synthesis of 5-(3-hydroxy-4-tetrahydropyranyloxy)-1-butynyl)-2,2'-bithiophene

To the mixture of 6.7 g (39 mmole) of 4-(tetrahydropyranyloxy)-3-hydroxy-1-butyne, 20 ml of benzene and 5.75 g of 5-iodo-2,2'-bithiophene (20 mmole) was added 0.15 g of CuI (0.796 mmole) and 0.14 g of benzyltriethylammonium chloride (0.63 mmole), 0.46 g of Pd(PPh$_3$)$_4$ (0.398 mmole) and 30 ml of NaOH solution (2.5N) under room temperature and stirred for 2 hours. 10 ml of NH$_4$Cl solution was then added. The reaction mixture was extracted with ethyl acetate and washed with 10 ml of HCl (10%) for 3 times, 50 ml of water for 3 times and dried over anhydrous magnesium sulfate. After evaporation of solvent the crude product was purified by silica gel column chromatography. From the eluate of ethyl acetate/n-hexane (1/3), 6.25 g of reddish oily product (95%) was obtained.

Data of Spectra:

$^1$H-NMR (CDCl$_3$): δ value 1.4–1.9 (m, 6H, 3CH$_2$) 3.3–4.0 (m, 4H, 2—OCH$_2$—) 4.5–4.7 (m, 1H, CH) 6.9–7.2 (m, 5H, protons of thiophene)

IR (neat): cm$^{-1}$ 3400 (OH), 2950(C—H), 2250(C≡C)

Mass: m/e (relative intensity) 334(80, M$^+$), 304(41), 234(49), 190(51), 86(100)

EXAMPLE 86

Synthesis of 5-(3-acetoxy-4-(2-tetrahydropyranyloxy)-1-butynyl)-2,2'-bithiophene To the mixture of 4.73 g of 3-acetoxy-4-tetrahydropyranyloxy-1-butyne (16.1 mmole), 15 ml of benzene and 5.15 g of 5-iodo-2,2'-bithiophene (24.2 mmole) was added 0.13 g of CuI, 0.12 g of benzyltriethylammonium chloride, 0.4 g of Pd(PPh$_3$)$_4$ and 20 ml of NaOH solution (2.5N) at room temperature and stirred for 2 hours. Then 8 ml of saturated NH$_4$Cl solution was added. The reaction mixture was extracted with ethyl acetate. The extract was washed with 10 ml of HCl (10%) twice, 50 ml of water twice and dried over anhydrous magnesium sulfate. After removal of solvent, the residual solid was purified by silica gel column chromatography. From the eluate of ethyl acetate/n-hexane (1/3) 4.1 g of desired orange yellow product (67%) was obtained first and 1.4 g of orange red oily product (23%) was eluted second as by-product.

Data of Spectra:

$^1$H-NMR (CDCl$_3$): δ value 1.4–1.9 (m, 6H, 3CH$_2$) 2.1 (s, 3H, —OCOCH$_3$) 3.7–4.0 (m, 4H, 2—OCH$_2$—) 4.7–4.8 (s, 1H, OCHO) 5.7–5.9 (m, 1H, CH) 7.0–7.3 (m, 5H, protons of thiophene)

IR (neat): cm$^{-1}$ 2950 (C—H), 2225 (C≡C), 1750 (C═O)

Mass: m/e (relative intensity) 376 (M$^+$, 69), 333(21), 275(30), 234(100)

EXAMPLE 87

Synthesis of 5-(3-acetoxy-4-hydroxy-1-butynyl)-2,2'-bithiophene 2.8 g (9.6 mmole) of 5-(3-acetoxy-4-tetrahydro-pyranyloxy-1-butynyl)-2,2'-bithiophene was dissolve 40 ml of methanol. 3 ml of H$_2$SO$_4$ solution (2N) was added slowly in ice bath and stirred at room temperature for 2 hours. The reaction solution was extracted with ethyl acetate. The extract was then washed with 10 ml of NaHCO$_3$ solution three time, 50 ml of water twice and dried over anhydrous magnesium sulfate. After removal of solvent, residual solid was purified by silica gel column chromatography. From the eluate of ethyl acetate/n-hexane (1/3) 1.83 g of oily product (84%) was obtained.

Data of Spectra:

$^1$H-NMR (CDCl$_3$): δ value 2.15 (s, 3H, —CH$_3$) 3.90 (d, 2H, —CH$_2$) 5.71 (t, 1H, CH) 7.0–7.3 (m, 5H, protons of thiophene)

IR (neat): cm$^{-1}$ 3450 (OH), 2250 (C≡C), 1730 (C═O)

EXAMPLE 88

Synthesis of 5-(3,4-dihydroxy-1-butynyl)-2,2'-bithiophene 6.15 g (18.4 mmole) of 5-[3-acetoxy-4-(tetrahydro-2-pyranyloxy)-1-butynyl)-2,2'-bithiophene was dissolved in 90 ml of methanol. 7 ml of H$_2$SO$_4$ solution (2N) was added slowly in ice bath and stirred at room temperature for 2 hours. The reaction solution was extracted with ethyl acetate. The extract was then washed with 10 ml of NaHCO$_3$ solution three time, 50 ml of water twice, over-saturated NaCl solution (20 ml) twice and dried over anhydrous magnesium sulfate. After removal of solvent, residual solid was purified by silica gel column chromatography. From the eluate of ethyl acetate/n-hexane (1/1) 3.0 g of dark yellow product (62%) was thus obtained. The melting point thereof was 105° C.

Data of Spectra:

$^1$H-NMR (CDCl$_3$): δ value 3.8 (d, 2H, CH$_2$) 4.7 (t, 1H, CH) 7.0–7.3 (m, 5H, protons of thiophene)

Mass: m/e (relative intensity) 250 (M$^+$, 78), 219 (100), 189 (1)

EXAMPLE 89

Synthesis of 5-(3,4-diacetoxy-1-butynyl)-2,2'-bithiophene 1.83 g (6.27 mmole) of 5-(3-acetoxy-4-hydroxy) -1-butynyl-2,2'-bithiophene was dissolved in 1.5 g (18.81 mmole) of pyridine with 1.27 g (12.54 mmole) of acetic anhydride at room temperature and stirred for 2 hours. The reaction solution was extracted with ethyl acetate. The extract was washed with 10 ml of HCl (10%) for 3 times, 10 ml of KHCO$_3$ solution for three times and 50 ml of water twice. The solution was then dried over anhydrous magnesium sulfate. After removal of solvent, the residual solid was purified by silica gel column chromatography. From the eluate of ethyl acetate/n-hexane (1/5). 1.91 g of greenish yellow oily product (91%) was obtained.

Data of Spectra:

$^1$H-NMR (CDCl$_3$): δ value 2.07 (s, 3H, —CH$_3$) 2.12 (s, 3H, —CH$_3$) 4.25–4.45 (m, 2H, CH$_2$) 5.80–5.87 (m, 1H, CH) 7.0–7.3 (m, 5H, protons of thiophene)

IR (neat): cm$^{-1}$ 2250 (C≡C), 1755 (C═O), 1735 (C═O)

Mass: m/e (relative intensity) 334 (M$^+$, 75), 274(100) 232(55)

EXAMPLE 90

Synthesis of 5-(3,4-diisovaleryloxy-1-butynyl)-2,2'-bithiophene 0.44 g (1.76 mmole) of 5-(3,4-dihydroxy-1-butynyl)-2,2'-bithiophene was dissolved in 10 ml of dichloromethane containing 0.7 ml of pyridine. The reaction solution was then mixed with 1.0 g of isovaleryloxy chloride previously dissolved in 10 ml of dichloromethane in ice bath, and stirred for ½ hour. The solution was extracted with dichloromethane, washed with 10 ml of HCl (10%) twice, 10 ml of KHCO$_3$ solution for three times and 50 ml of water twice. The solution was then purified by silica gel column chromatography. From the eluate of n-hexane/ethyl acetate (9/1). 0.5 g of yellowish green liquid diester was obtained; and from the eluate of n-hexane/ethyl acetate (3/1), dark yellow mixture of monoester was obtained.

EXAMPLE 91

Synthesis of 5-(3,4-distearyloxy-1-butynyl)-2,2'-bithiophene 170 mg (0.68 mmole) of 5-(3,4-dihydroxy-1-butynyl)-2,2-bithiophene was dissolved in a mixture of 10 ml of dichloromethane and 0.2 ml of pyridine. 0.7 g of stearoyl chloride dissolved in 10 ml of dichloromethane was then dropped into the reaction mixture in ice bath. This reaction solution was stirred for 2 days. It was monitored by thin layer chromatography to determine if there were 3 products obtained, i.e. a mixture of 1 diester and 2 monoesters.

EXAMPLE 92

Synthesis of 5-(3,4-dibenzoxy-1-butynyl)-2,2'-bithiophene 0.64 g (2.56 mmole) of 5-(3,4-dihydroxy-1-butynyl)-2,2'-bithiophene was dissolved in 10 ml of dichloromethane containing 0.7 ml of pyridine. The reaction solution was then mixed with 0.8 g of benzoyl chloride previously dissolved in 10 ml of dichloromethane in ice bath and stirred for 2 hours. The solution was extracted with dichloromethane, washed with 10 ml of HCl (10%) twice, 10 ml of KHCO$_3$ solution for three times and 50 ml of water twice. The solution was then purified by silica gel column chromatography. The ratios of n-hexane/ethyl acetate as eluant were respectively 9/1, 4/1, 3/1 and the greenish yellow solid (diester-benzyl ester), dark yellow liquid (1-benzyl ester), dark red liquid (2-benzyl ester) were thus respectively obtained.

EXAMPLE 93

Synthesis of 5,5'-dihydroxymethyl-2,2'-bithiophene (1) 0.2 g of 5-hydroxymethyl-5'-formyl-2,2'-bithiophene was dissolved in 50 ml of ethanol. 0.1 g of NaBH$_4$ was added at room temperature and stirred for 1 hour. The solution was monitored by thin layer chromatography to determine whether the reaction was completed. H$_2$O (50 ml) was added and the ethanol was removed under reduced pressure. After filtration, the slight yellowish solid product was obtained. The yield was almost quantitative and the melting point of the product was 158°–160° C.

Data of spectra:
$^1$H-NMR (d$^6$-acetone): δ 7.03–6.87 (m, 4H, protons of thiophene) 4.73 (s, 4H, —CH$_2$OH)

IR (KBr): cm$^{-1}$ 3500–3300 (OH) 2909, 2850 1453, 1415, 1360, 1230, 1200, 1175 1055, 1025, 1002 880, 870, 795

Mass: m/e (relative intensity) 226 (M$^+$, 100), 209 (M$^+$—OH, 73)

(2) 0.6 g of 5-formyl-5'-hydroxymethyl-2,2'-bithiophene was dissolved in 30 ml of tetrahydrofuran. 0.16 g of NaBH$_4$ was then added and the solution was stirred for 2 hours at room temperature. THF was removed under reduced pressure. The white solid obtained was washed with water and dried under reduced pressure. The yield was quantitative. The melting point of the product was 155°–156° C.

(3) 0.5 g of 5-formyl-5'-hydroxymethyl-2,2'-bithiophene was reduced in 75 ml ethanol with 0.3 g NaBH$_4$. The mixture was stirred for 3 hours at room temperature. The solution was concentrated and n-hexane was added to crystallize the white-powdered product. The crystal was filtered and washed with water. It was dried under reduced pressure and the yield was quantitative. The melting point of the product was 155°–156° C.

(4) 5,5'-Dihydroxymethyl-2,2'-bithiophene was also obtained by refluxing 2-hydroxy-methyl-5-iodo-thiophene with Cu powder in dimethyl formamide. The Ullmann condensation yielded a very poor amount of 5,5'-dihydroxymethyl-2,2'-bithiophene.

(5) The Ullmann condensation of 2-acetoxymethyl-5-iodothiophene gave 5,5'-diacetoxymethyl-bithiophene. The 5,5'-dihydroxymethyl-2,2'-bithiophene was obtained by alkaline hydrolysis of the diacetoxy compound and refined by column chromatography. The yield was about 20%.

EXAMPLE 94

Synthesis of 5,5'-diacetoxymethyl-2,2'-bithiophene 0.23 g of 5,5'-dihydroxymethyl-2,2'-bithiophene, pyridine (1.2 ml) and acetic anhydride (0.3 ml) were mixed with stirring and kept overnight. Then the mixture was extracted with ethylacetate. The pyridine and acetic acid were removed by washing with weak base, weak acid and water, respectively. Silica gel powder was added into the ethyl acetate solution and the solvent was removed under reduced pressure. Coated silica gel powder was added to the silica gel column and chromatographed. From the eluate of ethyl acetate/n-hexane (7/3) white platelet crystal thus obtained was further recrystallized with ethyl acetate/n-hexane mixture. The melting point of the product was 60° C.

Data of spectra:
IR: cm$^{-1}$ 1725 (C=O)

Mass: m/e (relative intensity) 310 (M$^+$, 37) 251 (M$^+$—CH$_3$CO$_2$, 100) 192 (M$^+$—2CH$_3$CO$_2$, 34)

EXAMPLE 95

Synthesis of 5-formyl-5'-hydroxymethyl-2,2'-bithiophene 1 ml of POCl$_3$ was added into 20 ml DMF slowly under nitrogen gas atmosphere in ice bath and stirred for 1 hour. The DMF solution 0.5 g of 5-hydroxymethyl-2,2'-bithiophene (0.5 g) was dropped in slowly. The mixture was stirred for half an hour at room temperature, then the temperature was raised to 50° C. and was further stirred for 3 hours. The reaction solution was poured into potassium carbonate ice water solution. Then the solution was extracted with 100 ml of ethyl acetate. The extract was washed with water and dried over anhydrous magnesium sulfate. The solvent was removed under reduced pressure. The residual solid was purified by column chromatography. From the eluate of ethyl acetate/n-hexane (3/7) slightly yellowish product was obtained. It was further recrystallized from ethyl acetate/n-hexane mixture. The melting point of the product was 123°–124° C. The yield was 85%.

Data of Spectra:
$^1$H-NMR 400 MHz (CDCl$_3$): δ value 9.91 (s, 1H, —CHO) 7.73–7.02 (m, 4H, protons of thiophene) 4.91–4.90 (d, 2H, —CH$_2$OH)

IR (KBr): cm$^{-1}$ 3300 (OH) 1640 (C=O)

Mass: m/e (relative intensity) 224 (M$^+$, 100) 207 (M$^+$, —OH, 57) 195 (M$^+$, —OH—, —CHO, 22)

EXAMPLE 96

Synthesis of 5-acetoxymethyl-5'-formyl-2,2'-bithiophene 0.2 g of 5-formyl-5'-hydroxymethyl-2,2'-bithiophene and 1 ml of pyridine were mixed together. 1 ml of acetic anhydride was added slowly into the mixture and stirred for 2 hours. 200 ml of ethyl acetate and 50 ml of water were then added and the ethyl acetate layer was washed with weak base, weak acid and water. The solvent was removed and the product was purified by column chromatography. From the eluate of ethyl acetate/n-hexane (1/9) slightly yellowish crystal was obtained. The melting point of the crystal was 89°–91° C. The yield was 95%.

Data of Spectra:
$^1$H-NMR 400 MHz (CDCl$_3$): δ value 9.83 (s, 1H, —CHO) 7.64–7.01 (m, 4H, protons of thiophene) 5.20 (s, 2H, —C$\underline{H}_2$OAc) 2.08 (s, 3H, —COC$\underline{H}_3$)
IR (KBr): cm$^{-1}$ 1740, 1660 (C=O)

EXAMPLE 97

Synthesis of 5-formyl-5"-hydroxymethyl-2,2':5',2"-terthiophene 1 ml of POCl$_3$ was added to 30 ml of DMF slowly under nitrogen stream in ice bath temperature. The solution was stirred for 0.5 hour and then 20 ml DMF solution of 0.3 g of 5-hydroxymethyl-2,2':5',2"-terthiophene was dropped in slowly. The mixture was stirred for one hour at room temperature and then the temperature was raised to 60° C. and stirred for further 2 hours. The reaction solution was poured into ice aqueous potassium carbonate solution. The solution was extracted with 300 ml of ethyl acetate and the extract was washed with water. The solvent was removed under reduced pressure and the residual solid was purified by column chromatography. From the eluate of ethyl acetate/n-hexane (3/7) the orange crystal was obtained and the melting point of the product was 176°–177° C. The yield was 80%.

Data of Spectra:
$^1$H-NMR 400 MHz (CDCl$_3$): δ value 9.86 (s, 1H, —C$\underline{H}$O) 7.65–6.91 (m, 6H, protons of thiophene) 4.80 (s, 2H, —C$\underline{H}_2$OH)
IR (KBr): cm$^{-1}$ 3400 (OH) 1660 (C=O)
Mass: m/e (relative intensity) 306 (M$^+$, 100) 289 (M$^+$, —OH 56)

EXAMPLE 98

Synthesis of 5,5"-dihydroxymethyl-2,2':5',2"-terthiophene 1 g of 5,5"-diformyl-2,2':5',2"-terthiophene was added into 150 ml of THF. The temperature was raised to 50° C. until the solid was completely dissolved, then 0.25 g of NaBH$_4$ was added and stirred for 3 hours at 50° C. The THF solvent was removed under reduced pressure. Ethyl acetate and water were added to dissolve the residual solid. The ethyl acetate layer was washed with water and dried over anhydrous magnesium sulfate. The ethyl acetate layer was filtered and concentrated to obtain 0.95 g slightly yellowish crystal and the melting point of the product was 182°–183° C.

Data of Spectra:
$^1$H-NMR 400 MHz (CDCl$_3$): δ value 7.04–6.89 (m, 6H, protons of thiophene) 4.79 (d, 4H, C$\underline{H}_2$OH) 1.51 (br.s., OH)
Mass: m/e (relative intensity) 308 (M$^+$,58) 306 (M$^+$—2H, 100)

EXAMPLE 99

Synthesis of 5-hydroxymethyl-5"-(1-hydroxypropyl)-2,2':5',2"-terthiophene (1) 0.5 ml of POCl$_3$ was added to 30n ml of DMF slowly under nitrogen stream in ice bath condition. The solution was stirred for 1 hour and 20 ml of DMF solution of 0.8 g of hydroxymethyl-terthiophene was dropped in slowly. Then the solution was heated to 70° C. with oil bath for 3 hours. The reaction solution was placed into 50 ml of aqueous K$_2$CO$_3$ solution at 0° C. The solution was extracted with 500 ml of ethyl acetate and treated in situ through purification by column chromatography. From the fraction of ethyl acetate/n-hexane (3/7) eluate the crude formyl derivative was obtained. After removal of solvent, the crude product was dissolved in 50 ml of THF under nitrogen stream and dropped in 1 ml of ethyl Grignard reagent and stirred at room temperature for 3 hours. The solution was monitored by thin layer chromatography to determine whether the reaction was completed. Then the solution was extracted with 300 ml of ethyl acetate and washed with water. After removal of solvent, the residual solid was purified by column chromatography. From the eluate of ethyl acetate/n-hexane (3/7) orange powder was obtained and the melting point of the product was 131° C.

(2) 0.5 g of 5-formyl-5"-hydroxymethyl-2,2':5',2"-terthiophene was dissolved in 50 ml of anhydrous THF. A little excess of calculated amount of ethyl magnesium bromide (2.0M) were added to the THF solution under nitrogen atmosphere. The solution was stirred for 3 hours at room temperature. Aqueous ammonium chloride solution was added to hydrolyze the above reaction solution to obtain the product. The solid was collected and purified by column chromatography. From the eluate of ethyl acetate/n-hexane (3/7) orange powdered crystal 0.3 g was obtained. The melting point was 131°–132° C.

Data of spectra:
$^1$H-NMR 400 MHz (CDCl$_3$): δ value 7.03–6.85 (m, 6H, protons of thiophene) 4.79–4.78 (m, 3H, —C$\underline{H}_2$OH and —C$\underline{H}$C$_2$H$_5$) OH 1.91–1.77 (m, 2H, —C$\underline{H}_2$CH$_3$) 0.99–0.95 (t, 3H, —C$\underline{H}_3$)
IR (KBr): cm$^{-1}$ 3400 (OH), 2900 (saturated CH)

EXAMPLE 100

Synthesis of 5-formyl-5"-(1-hydroxypropyl)-2,2':5',2"-terthiophene 0.8 g of 5-(1-hydroxypropyl)-2,2':5',2"-terthiophene, 2 ml of pyridine and 2 ml of acetic anhydride were mixed together and stirred for 2 hours. 100 ml of ethyl acetate and aqueous K$_2$CO$_3$ solution were added for extraction and the extract was washed by dilute HCl twice and H$_2$O twice. Acetate derivative was obtained from column chromatographic separation. The compound and 0.5 ml of POCl$_3$ were added into DMF (50 ml) slowly under nitrogen stream in ice bath condition. The mixture was stirred for 1 hour at room temperature and above obtained acetate dissolved in 15 ml DMF was dropped in, then the temperature was raised to 70° C. and stirred for further 3 hours. The reaction solution was poured into a mixture of ethyl acetate (200 ml) and aqueous K$_2$CO$_3$ solution (50 ml). The solution was then purified by column chromatography. The product thus obtained was added into 50 ml of methanol containing NaOH (4N) and heated to refluxing. After dilution with H$_2$O, the precipitate was filtered. The melting point of the product was 125° C.

EXAMPLE 101

Synthesis of 5-(3-carboxypropionyloxymethyl)-2,2'-bithiophene 2.5 g of 5-hydroxymethyl-2,2'-bithiophene, 20 ml of pyridine and 1.2 g of succinic anhydride were mixed together and stirred at 40° C. Thin layer chromatography was applied to monitor the reaction. After the reaction was completed, ethyl acetate (200 ml) and diluted hydrochloric acid was added for neutralization. The reaction solution was then washed with water and aqueous sodium bicarbonate. The ethyl acetate layer was dried over anhydrous magnesium sulfate, condensed to saturation and then mixed with large amount of n-hexane for crystallization. 2.43 g of white crystal was then obtained and the melting point thereof was 112° C.

Data of spectra:
$^1$H-NMR (CDCl$_3$): δ value 7.20–6.90 (m, 5H, protons of thiophene) 5.23 (s, 2H, —C$\underline{H}_2$O—) 2.69–2.61 (m, 4H, —COC$\underline{H}_2$C$\underline{H}_2$CO—) 2.40 (br, OH)
IR (KBr): cm$^{-1}$ 3200–2500 (OH) 1720, 1690 (C=O)

EXAMPLE 102

Synthesis of 5,5'-bis-(3-carboxypropionyloxymethyl)-2,2'-bithiophene 0.5 g of 5,5'-dihydroxymethyl-2,2'-bithiophene, 10 ml of pyridine and 2 g of succinic anhydride were mixed together. The mixture was stirred at 40° C. Thin layer chromatography was applied to monitor the reaction. After the reaction was completed, ethyl acetate was added to extract the product. The ethyl acetate layer was washed with diluted hydrochloric acid and water to remove pyridine completely. The product was filtered through silica gel powder layer and the solid obtained upon removal of solvent, was recrystalized with ethyl acetate/n-hexane mixture. White crystal (0.45 g) was obtained and the melting point thereof was 137° C.

Data of spectra:
$^1$H-NMR 400 MHz (CDCl$_3$): δ value 7.00–6.90 (m, 4H, protons of thiophene) 5.28–5.23 (m, 4H, —C$\underline{H}_2$O—) 4.78–4.75 (m, 4H, —C$\underline{H}_2$O—) 2.69–2.64 (m, 8H, —CO—C$\underline{H}_2$C$\underline{H}_2$—CO—) —COC$\underline{H}_2$C$\underline{H}_2$CO—)
IR (KBr): cm$^{-1}$ 3600–2500 (OH) 1718, 1688 (C=O)

EXAMPLE 103

Synthesis of 5-formyl-5'-(3-carboxypropionyloxymethyl)-2,2'-bithiophene 0.63 g of 5-hydroxymethyl-5'-formyl-2,2'-bithiophene, 10 ml of pyridine and 0.12 g of succinyl anhydride were mixed together. The mixture was stirred at 40° C. Thin layer chromatography was applied to monitor the reaction. After the reaction was completed, diluted hydrochloric acid and ethyl acetate were added. The ethyl acetate solution was washed with water to remove pyridine completely. Then the ethyl acetate layer was dried over anhydrous magnesium sulfate and filtered through silica gel layer. After removal of the solvent, the product was recrystallized with ethyl acetate/n-hexane mixture to give a slightly yellowish crystal (0.6 g). The melting point was 127° C.

Date of Spectra:
$^1$H-NMR 400 MHz, (CDCl$_3$): δ value 9.8 4 (s, 1H, —C$\underline{H}$O) 7.65–7.02 (m, 4H, protons of thiophene) 5.25 (s, 2H, —C$\underline{H}_2$O—) 2.72–2.64 (m, 4H, —COC$\underline{H}_2$C$\underline{H}_2$CO—) 2.40 (br, OH)
IR (KBr): cm$^{-1}$ 3200–2500 (OH) 1730, 1705, 1650 (C=O)

EXAMPLE 104

Anti-edema animal test

Anti-edema activity of *Echinops grijissi* extract and various compounds within the scope of the present invention was tested according to the conventional toe edema method as described in Winter, et al., *Biol. Med.*, 111, 544 (1962); and Roszkowski, et al. *J. Pharmcol. Exp. Ther.*, 179, 114 (1971) (both hereby incorporated by reference), using carrageenan as pyrogen (Sigma Chem. Co., No. C-3889, Type IV, Lambda-Carrageenan) and indomethacin (Sigma Chem. Co.) as a control inhibitory agent. Note that the anti-edema test is a method of screening for anti-inflammatory compounds. The results of the use of the compounds of the instant invention were compared with those of indomethacin. The inhibitory effect of conventional anti-inflammatory drugs was in the range of 20 to 40% and that of indomethacin was at best, 40%. If the test results showed an inhibitory efficiency of about or above 30%, the compound tested was considered to have significant anti-edema effects.

Results are illustrated in Tables 1 and 2.

Table 1 illustrates the test results of extracts from *Echinops grijissii*. These results reveal the obvious anti-edema effect of fractions extracted with the nonpolar solvent, ethyl acetate and ethanol.

Table 2 illustrates the results of synthetic thiophene derivatives tested in various dosages. The anti-edema efficiencies of these synthetic thiophene derivatives are similar to those of the natural *Echinops grijisii* extracts. Thiophene derivatives with substituents at the 2- or 5- position had higher activities. Note that in Table 2, the symbol "*" indicates observation of symptoms of intoxication.

TABLE 1

Results of Anti-edema test for *Echinops grijisii* extract

| | Test fraction | Dosage mg/kg Rat | Inhibition rate % | Test fraction (Et$_2$ O extract via Si-gel column fractionation) | | Dosage mg/kg Rat | Inhibition rate % |
|---|---|---|---|---|---|---|---|
| Hydrophobic fraction | Et$_2$ O Extract | 1.0 | 50 | n-Hexane eluate | Crude | 10 | 48 |
| | | | | | Mixture | 100 | 20* |
| | | 10 | 31 | | Major Component | 100 | 35* |
| | | | | | Minor Component | 100 | 43 |
| | | 100 | 34 | EtOAc eluate | | 10 | 63 |
| | | | | | | 100 | 70 |
| | | | | EtOH eluate | | 10 | 46 |
| | | | | | | 100 | 35 |
| | EtOAc Extract | 100 | 58 | | | | |
| Hydrophilic fraction | Fraction insoluble in Et$_2$ O & EtOAC extraction | 100 | 13 | | | | |
| | | 1000 | 22 | | | | |
| | | 1000 | 22 | | | | |
| | | 2000 | 46 | | | | |

Note: * indicates rats have been toxicated

TABLE 2

Results of anti-edema test for synthetic thiophene derivatives

| Compound | Dosage (mg/kg) | Inhibition rate (%) |
|---|---|---|
| 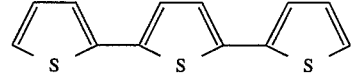 | 10<br>50<br>100<br>200 | 18<br>15<br>19<br>22 |
| 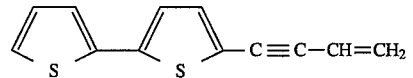 | 10<br>50<br>100 | 22<br>37<br>44 |
| 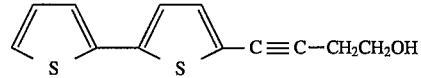 | 50<br>100<br>200*<br>500* | 32<br>36<br>38<br>52 |
| 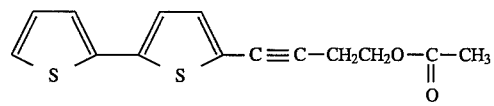 | 10<br>100<br>200 | 32<br>52<br>39 |
| 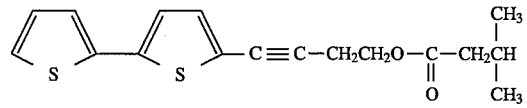 | 1<br>10<br>50<br>100<br>150 | 15<br>26<br>31<br>37<br>52 |
| 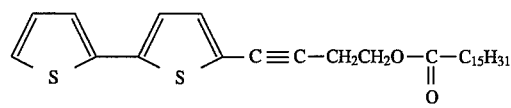 | 50<br>100<br>200 | 37<br>33<br>31 |
| 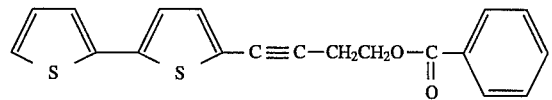 | 10<br>50<br>100<br>200 | 31<br>37<br>49<br>30 |
| 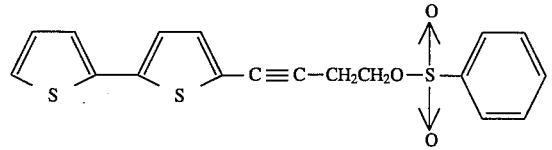 | 10<br>50<br>100 | 37<br>36<br>36 |
| 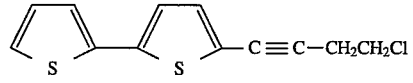 | 10<br>50<br>100<br>200 | 28<br>42<br>Toxic<br>Toxic |
| 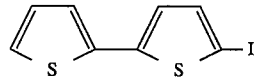 | 10<br>50<br>100 | 31<br>30<br>34 |
| 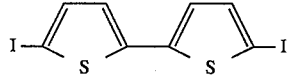 | 100<br>200<br>500 | 21<br>23<br>30 |
| 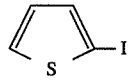 | 10<br>50<br>100<br>200 | 8<br>19<br>25<br>— |
| 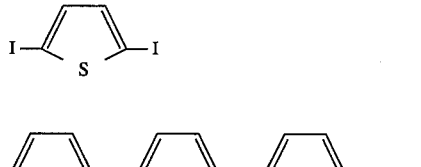 | 10<br>50<br>100<br>200<br>500 | 24<br>43<br>42<br>42<br>27 |
| 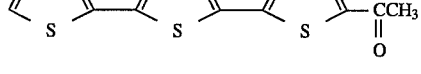 | 10<br>50<br>100<br>200<br>500 | 16<br>24<br>26<br>32<br>28 |

TABLE 2-continued

Results of anti-edema test for synthetic thiophene derivatives

| Compound | Dosage (mg/kg) | Inhibition rate (%) |
|---|---|---|
| 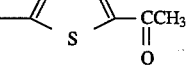 | 10<br>50<br>100<br>200 | 18<br>23<br>26<br>33 |
| 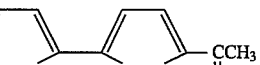 | 1<br>10<br>50<br>100<br>200 | 18<br>28<br>31<br>23<br>25 |
|  | 0.1<br>0.5<br>1<br>5<br>*10<br>*50<br>*100 | 28<br>32<br>22<br>29<br>(76)<br>(86)<br>(81) |
| 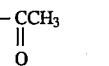 | 50<br>100<br>200 | 12<br>31<br>18 |
|  | 50<br>100<br>200 | 17<br>24<br>22 |
| 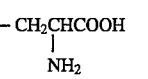 | 10<br>50<br>100<br>200 | 27<br>27<br>40<br>27 |
|  | 50<br>100<br>200 | 4<br>23<br>35 |
| 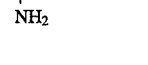 | 10<br>50<br>100<br>200 | 26<br>34<br>37<br>41 |
|  | 10<br>50<br>100<br>200<br>500 | 8<br>17<br>28<br>28<br>28 |
|  | 10<br>50<br>100<br>200 | 22<br>—<br>37<br>50 |
|  | 10<br>50<br>100<br>200 | 5<br>17<br>22<br>18 |
|  | 10<br>50<br>100 | 44<br>33<br>39 |

TABLE 2-continued

Results of anti-edema test for synthetic thiophene derivatives

| Compound | Dosage (mg/kg) | Inhibition rate (%) |
|---|---|---|
| pyridine-pyridine-pyridine (terpyridine) | 10<br>50<br>100 | 10<br>Toxic<br>Toxic |
| tetrathiophene | 10<br>50<br>100<br>200 | —<br>20<br>19<br>28 |
| O₂N—[thiophene]—COOH | 10<br>50<br>100 | 29<br>22<br>30 |
| O₂N—[thiophene]—CHO | 10<br>50<br>100 | 35<br>20<br>Toxic |
| CH₃—[thiophene]—CH₃ | 10<br>50<br>100<br>200 | 30<br>30<br>30<br>28 |
| benzothiophene | 10<br>50<br>100 | 26<br>30<br>30 |
| [thiophene]—OCH₃ | 10<br>50<br>100<br>200 | 16<br>15<br>29<br>14 |
| bithiophene | 10<br>50<br>100<br>200 | 23<br>43<br>41<br>46 |
| (CH₃)₃C-[benzoxazole]-N=CH-[thiophene]-CH=N-[benzoxazole]-C(CH₃)₃ | 50<br>100<br>200 | 32<br>17<br>negative |
| dibenzothiophene | 50<br>100<br>*200 | 28<br>45<br>55 |
| O₂N—[thiophene]—CH(OAc)₂ | 10<br>50<br>100<br>200 | 20<br>22<br>28<br>25 |
| [thiophene]—NO₂ | 10<br>*100<br>*200 | 18<br>9<br>(46)<br>— |
| [bithiophene]—NO₂ | 1<br>5<br>10<br>50<br>100<br>200 | 18<br>28<br>35<br>31<br>23<br>25 |
| [thiophene]—CH₂OH | 50<br>100<br>200 | 29<br>35<br>26 |

TABLE 2-continued

Results of anti-edema test for synthetic thiophene derivatives

| Compound | Dosage (mg/kg) | Inhibition rate (%) |
|---|---|---|
| 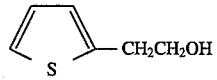 thiophene-CH₂CH₂OH | 50<br>100<br>200 | 29<br>35<br>31 |
|  thiophene | 50<br>100<br>200 | 20<br>20<br>15 |
| 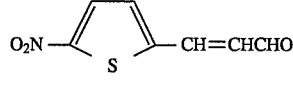 O₂N-thiophene-CH=CHCHO | 10<br>50<br>100<br>200 | —<br>37<br>37<br>33 |
| 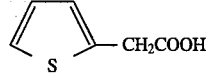 thiophene-CH₂COOH | 10<br>50<br>100<br>200 | —<br>14<br>16<br>36 |
| 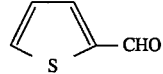 thiophene-CHO | 10<br>50<br>100<br>200 | 8<br>33<br>31<br>19 |
| 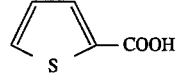 thiophene-COOH | 50<br>100<br>200 | 12<br>12<br>12 |
| 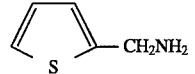 thiophene-CH₂NH₂ | 50<br>100<br>200 | 18<br>33<br>31 |
| 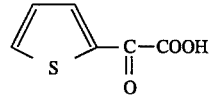 thiophene-C(=O)-COOH | 50<br>100<br>200 | 8<br>15<br>24 |
| 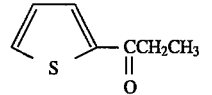 thiophene-C(=O)CH₂CH₃ | 50<br>100<br>200 | 18<br>53<br>74 |
| 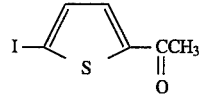 I-thiophene-C(=O)CH₃ | 1<br>10<br>100<br>200 | 18<br>16<br>23<br>26 |
| 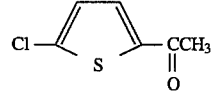 Cl-thiophene-C(=O)CH₃ | 10<br>*50<br>*100<br>*200 | 15<br>37<br>(51)<br>(81) |
| 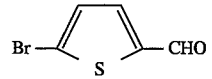 Br-thiophene-CHO | 50<br>100<br>*200 | 8<br>30<br>35 |
| 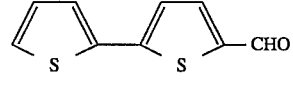 bithiophene-CHO | 10<br>50<br>100<br>200<br>500 | 10<br>11<br>19<br>50<br>36 |
| 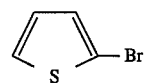 thiophene-Br | 10<br>50<br>100<br>200 | 21<br>33<br>34<br>34 |
| 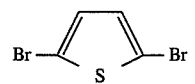 Br-thiophene-Br | 10<br>50<br>*100<br>*200 | 20<br>30<br>(67)<br>(73) |

TABLE 2-continued

Results of anti-edema test for synthetic thiophene deriratives

| Compound | Dosage (mg/kg) | Inhibition rate (%) |
|---|---|---|
| Br, Br on thiophene (S) | 10<br>*50<br>*100<br>*200 | 24<br>(61)<br>(81)<br>(95) |
| Br, Br, Br, Br on thiophene (S) | 10<br>50<br>100<br>200 | 20<br>14<br>10<br>18 |
| Cl, Cl on thiophene (S) | 10<br>*50<br>*100 | 10<br>(45)<br>(74) |

EXAMPLE 105

Interferon ("IFN") induction assay

The compounds to be tested were administered intraperitoneally in dosages of 1, 2.5, or 5 mg/kg/day to male C3H mice (8 weeks old), and sera were collected after 6, 24, or 48 hours. Each group included 4 mice. The IFN level was assayed by the cytopathic effect ("CPE") of Vesicular Somatic Virus ("VSV") in a 96-well microplate (Costar). Each well contained 0.1 ml of 2-fold-diluted serum and 0.1 ml of 7×10 L-929 cells in RPMi1640 (Gibco) with 10% fetal calf serum. The microplate was kept at 37° C. for 2 hours in 5% $CO_2$ and 95% air. After washing with the RPMI1640 medium, VSV of 100 ID in 0.1 ml of RPMI1640 with 1% calf serum was added to the cells. The infected cells were further incubated for 24 hours, in which control reached peak CPE. The reciprocal of serum dilution, which showed 50% inhibition of CPE, was calculated as IFN potency. The potency was corrected for international units by comparison with reference IFN: NIH (1-929-NDV).

Results are illustrated in Table 3.

TABLE 3

Results of Interferon inducing activity for fraction of *Echimops grijisii* extraction

| Serum dilution | Dosage mouse | | | | | | |
|---|---|---|---|---|---|---|---|
| | $Et_2$ O extract | | $H_2$ O Soluble fraction | | n-Hex eluate | EtOAc eluate | EtOH eluate |
| | 0.1 mg | 1 mg | 10 mg | 100 ng | 1 mg | 1 mg | 1 mg |
| 4 | − | − | + | + | − | − | − − |
| 8 | − | − | + | + | − | − | − − |
| 16 | − | − | + | + | + | − | − − |
| 32 | + | − | + | + | − | − | − − |
| 64 | + | − | + | + | − | − | − − |
| 128 | + | − | + | + | − | + | − − ++ |
| 256 | + | + | + | + | + | + | ++ −+ |
| 512 | + | + | + | + | − | − | − − +− |
| IF Calculated (L.U./ml) | 1<br>16X −<br>0.2 =<br>80 | 1<br>128X −<br>0.2 =<br>640 | 0 | 0 | 1<br>128X −<br>0.2 =<br>640 | 1<br>64X −<br>0.2 =<br>320 | 1<br>128X −<br>0.2 =<br>640 | 1<br>64X −<br>0.2 =<br>320 |

Note: IF (Laboratory unit/ml) = A × B
A: The highest serum dilution per well with less than 50% infected.
B: 1/Serum dilution per well (ml).
n-Hex eluate contains thionhene compounds a, b, c, d
EtOAc eluate contains thionhene compounds e, f, g, h, i
EtOH eluate contains thionhene compounds j

EXAMPLE 106

Granulocyte-macrophage colony stimulating activity

The proliferative response of granulocyte-macrophage colonies was evaluated on the basis of $H^3$-thymidine incorporation. Mouse fibroblast L929 cell conditioned medium was prepared as described in Hines, D., "Liquid Accumulation and Production of Colony-Stimulating Activity by the 266AD Cell Line Derived from Mouse's Bone Marrow", *Blood*, 61, 397–402, 1983 (hereby incorporated by reference) with minor modification. L929 cells ($1\times10^6$) were transferred to a 75 $cm^2$ tissue culture flask and cultured for 5 days with 10% fetal calf serum (FCS) at 37° C. in 5% $CO_2$ in air. Confluent cells were fed with fresh medium, and conditioned medium was removed after 24 hours. Cells were filtered with a millipore 0.22 membrane and stored at 20° C. until use. Male C3H/He mice were killed by cervical dislocation. Femoral bone marrow cells for culture and as a source of granulocyte/macrophage progenitor cells were obtained by flushing the marrow cavity with RPMI1640 medium using a 26-gauge needle. The cells ($4 \times 10^{5}$/ml) were cultured in a medium containing RPMI1640 with $5 \times 10^{-6}$M 2-mercaptoethanol, 100 units/ml benzylpenicillin, 100 ug/ml streptomycin, and 5% heat-inactivated FCS, in addition to a final 5% v/v concentration of mouse fibroblast L929 conditioned medium. 180 µl were then added to each well of flat-bottomed microplates (Costar), with or without test sample, and were incubated for 4 days at 37° C. in a humidified atmosphere containing 5% $CO_2$. 0.4 µCi of $H^3$—thymidine was subsequently added to each well 18 hours before cell harvest. The cells were frozen and thawed three times, collected, and washed with normal saline and 5% cold trichloracetic acid (E. Merk, Darmstadt, West Germany) in a multiple automated cell harvester. The incorporated radioactivity was measured using a liquid scintillation counter. All assay were performed in quadruplicate.

Results are illustrated in Table 4.

EXAMPLE 107

Proliferative response of mouse lymphocytes

Fresh splenocytes ($1 \times 10^6$ cells/ml) from male C3H/He mice were suspended in a medium containing RPMI1640 with 0.1 mM nonessential amino acid, $2 \times 10^{-6}$M 2-mercaptoethanol, 100 units/ml benzylpenicillin, 100 ug/ml streptomycin, and 10% heat-inactivated FCS in addition to a final concentration of 3 ug/ml of concanavalin A (Sigma Chem.). 180 µl of the suspensions were then added to each well of flat-bottomed microplates (Costar), with or without test compounds, and were incubated for 3 days at 37° C. in a humidified atmosphere containing 5% $CO_2$. 0.2 µCi of $H^3$-thymidine was subsequently added to each well 18 hours before cell harvest. The incorporated radioactivity was measured using a liquid scintillation counter. All assay were performed in quadruplicate.

Table 4 shows the biological assay, including granulocyte-macrophage colony stimulating activity and proliferative response of mouse lymphocytes, T-cell, for synthetic thiophene compounds.

TABLE 4

Results of proliferation stimlation activity of Granulocyte/Macrophage (G/M) and T-lymphocyte cells by synthetic thiophene derivatives

| Compound | Conc. | G/M Cell (from Bone Marrow) Act. Index | T-Cell (from Spleen) Act. Index |
|---|---|---|---|
| No. 1 | 10 µg/ml | 1.38567 | 1.08134 |
|  | 1 µg/ml | 2.69897 | 1.01275 |
|  | 0.1 µg/ml | 1.08016 | 1.29756 |
| No. 2 | 10 µg/ml | 1.59001 | 1.06380 |
|  | 1 µg/ml | 2.31122 | 1.11335 |
|  | 0.1 µg/ml | 1.49453 | 1.57061 |
| No. 3 | 10 µg/ml | 1.62566 | 0.96966 |
|  | 1 µg/ml | 2.05036 | 1.10341 |
|  |  | 1.53955 | 1.53643 |
| No. 4 | 10 µg/ml | 1.43441 | 1.08268 |
|  | 1 µg/ml | 1.77533 | 1.31439 |
|  |  |  | 1.74917 |
| No. 5 | 10 µg/ml | 1.28985 | 0.95233 |
|  | 1 µg/ml | 1.70653 | 1.05716 |
| No. 6 | 10 µg/ml | 0.83674 | 1.10467 |
|  | 1 µg/ml | 1.08590 | 1.21843 |
|  |  |  | 1.61022 |
| No. 7 | 10 µg/ml | 0.61503 | 0.93275 |

TABLE 4-continued

Results of proliferation stimlation activity
of Granulocyte/Macrophage (G/M) and T-lymphocyte
cells by synthetic thiophene derivatives

| Compound | Conc. | G/M Cell (from Bone Marrow) Act. Index | T-Cell (from Spleen) Act. Index |
|---|---|---|---|
| (bithiophene)–CH=C(Br)(Br) | 1 μg/ml<br>0.1 μg/ml | 0.66165<br>0.12152 | 1.54623<br>3.60099 |
| No. 8 (bithiophene)–CH=CH–C(=O)CH$_3$ | 10 μg/ml<br>1 μg/ml<br>0.1 μg/ml | 0.82208<br>1.78078<br>1.33562 | 1.92117<br>1.93501<br>1.82245 |
| No. 9 (bithiophene)–CH=CH–C(=O)–C(CH$_3$)(CH$_3$)(CH) | 10 μg/ml<br>1 μg/ml | 1.19032<br>1.58837 | 1.04911<br>0.94606<br>1.17593 |
| No. 10 (bithiophene)–C(=O)–CH=CH–(C$_6$H$_3$(OCH$_3$)(CH)) | 10 μg/ml<br>1 μg/ml | 1.11679<br>1.23538 | 0.70072<br>0.79308<br>1.00708 |
| No. 11 (bithiophene)–CH=CH–C(=O)–(C$_6$H$_4$)–CH | 10 μg/ml<br>1 μg/ml | 1.99390<br>1.77040 | 0.96830<br>0.61336 |
| No. 12 (bithiophene)–CH=CH–C(=O)–(thiophene) | 10 μg/ml<br>1 μg/ml<br>0.1 μg/ml | 1.59747<br>2.02695<br>1.40294 | 0.69153<br>0.78724<br>1.13418 |
| No. 13 (bithiophene)–C(=O)–CH=CH–(thiophene) | 10 μg/ml<br>1 μg/ml | 1.02274<br>1.61993 | 0.77960<br>0.95703<br>0.76464 |
| No. 14 (bithiophene)–CH=CH–CCH(OCH$_3$)(OCH$_3$)(=O) | 10 μg/ml<br>1 μg/ml | 0.52013<br>0.38852 | 0.79528<br>0.83616 |
| No. 15 (terthiophene)–CHO | 10 μg/ml<br>1 μg/ml<br>0.1 μg/ml | 1.07562<br>1.22991<br>0.90274 | 0.47875<br>1.17394<br>1.08177 |
| No. 16 OHC–(terthiophene)–CHO (quaterthiophene dialdehyde) | 10 μg/ml<br>1 μg/ml<br>0.1 μg/ml | 1.02717<br>1.28943<br>1.13611 | 1.41244<br>1.19396 |
| No. 17 (bithiophene)–CH$_2$OH | 10 μg/ml<br>1 μg/ml<br>0.1 μg/ml | 1.38698<br>1.58199<br>0.87300 | 0.26402<br>0.44967<br>0.97216 |
| No. 18 | 10 μg/ml | 1.34370 | 1.18306 |

TABLE 4-continued

Results of proliferation stimlation activity
of Granulocyte/Macrophage (G/M) and T-lymphocyte
cells by synthetic thiophene derivatives

| Compound | Conc. | G/M Cell (from Bone Marrow) Act. Index | T-Cell (from Spleen) Act. Index |
|---|---|---|---|
| 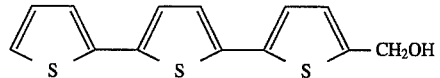 CH₂OH | 1 µg/ml<br>0.1 µg/ml | 1.59354<br>1.34150 | 1.61768<br>0.80177 |
| No. 19 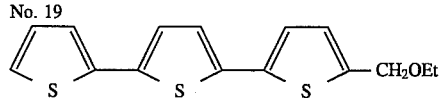 CH₂OEt | 10 µg/ml<br>1 µg/ml<br>0.1 µg/ml | 1.96969<br>2.68107<br>2.10073 | 1.25622<br>1.22816<br>0.84212 |
| No. 20 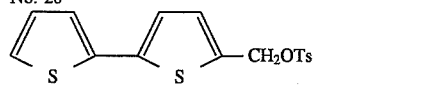 CH₂OTs | 10 µg/ml<br>1 µg/ml<br>0.1 µg/ml | 1.92896<br>1.58775<br>1.17211 | 1.27235<br>0.83798<br>1.13667 |
| No. 21 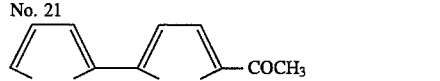 COCH₃ | 10 µg/ml<br>1 µg/ml<br>0.1 µg/ml | 1.12426<br>0.91394<br>0.87916 | 1.06133<br>0.93013<br>1.54280 |
| No. 22 CH₃CO—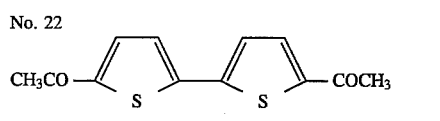—COCH₃ | 10 µg/ml<br>1 µg/ml | 3.44820<br>2.88312 | |
| No. 23 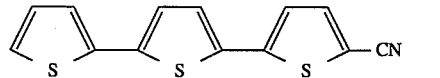 CN | 10 µg/ml<br>1 µg/ml<br>0.1 µg/ml | 0.85001<br>1.46072<br>0.89534 | 1.04615<br>1.62540<br>1.66646 |
| No. 24 NC——CN | 10 µg/ml<br>1 µg/ml<br>0.1 µg/ml | 1.60515<br>1.69135<br>1.55039 | 1.25060<br>1.41831<br>1.16228 |
| No. 25 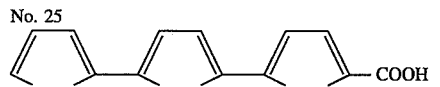 COOH | 10 µg/ml<br>1 µg/ml<br>0.1 µg/ml | 4.99874<br>4.90017<br>4.65231 | |
| No. 26 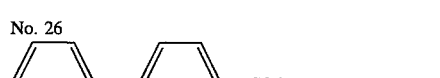 COOH | 10 µg/ml<br>1 µg/ml<br>0.1 µg/ml | 2.30172<br>2.53587<br>1.69505 | 1.24683<br>1.06895<br>1.06600 |
| No. 27 I—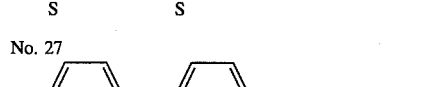—I | 10 µg/ml<br>1 µg/ml<br>0.1 µg/ml | 2.32175<br>2.24982<br>1.50722 | |
| No. 28 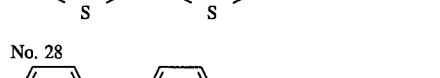 CH=CH—COOH | 10 µg/ml<br>1 µg/ml<br>0.1 µg/ml | 3.86843<br>5.16154<br>4.80503 | |
| No. 30 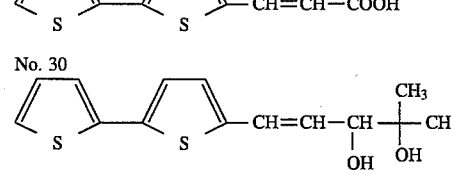 CH=CH—CH(OH)—C(CH₃)₂OH | 10 µg/ml<br>1 µg/ml<br>0.1 µg/ml | 0.59100<br>0.90660<br>1.40513 | |
| No. 31 | 10 µg/ml | | 0.79882 |

TABLE 4-continued

Results of proliferation stimlation activity
of Granulocyte/Macrophage (G/M) and T-lymphocyte
cells by synthetic thiophene derivatives

| Compound | Conc. | G/M Cell (from Bone Marrow) Act. Index | T-Cell (from Spleen) Act. Index |
|---|---|---|---|
| 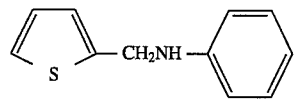 | 1 µg/ml<br>0.1 µg/ml | | 1.45705<br>1.23553 |
| No. 32 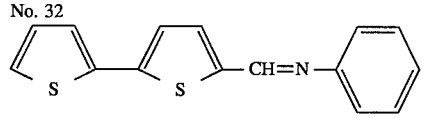 | 10 µg/ml<br>1 µg/ml<br>0.1 µg/ml | | 0.80565<br>1.45430<br>1.60137 |
| No. 33 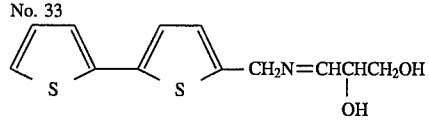 | 10 µg/ml<br>1 µg/ml<br>0.1 µg/ml | 1.41155<br>1.66912 | 1.03516<br>1.23227<br>1.20161 |
| No. 34 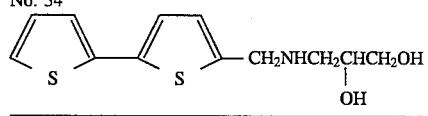 | 10 µg/ml<br>1 µg/ml<br>0.1 µg/ml | 0.55830<br>0.84330 | 2.30425<br>1.21408 |

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of treating inflammation comprising administering to a subject in need thereof a pharmaceutical composition which contains an effective amount of a compound of the following formula:

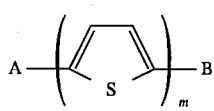

wherein m is 2–4; and each of A and B, independently, is H, $C_{1-7}$ alkyl, $C_{2-7}$ alkenyl, $C_{2-7}$ alkynyl, $(CH_2)_nCHO$, $(CH_2)_oCOOH$, $C_{1-7}$ alkoxy, $C_{2-7}$ alkoxyalkyl, $C_{1-7}$ hydroxyalkyl, CN, $NO_2$, halogen, $CH(OR^1)$ $CO.R^1$, $NR^2R^3$ or its acid salt, $CO.NR^2R^3$, $CHR^1NR^2R^3$ or its acid salt, $CH=NR^2$, $C\equiv CR^4$, $CR^1=CR^5R^6$, $CO.CH=CHR^7$, $CH=CHR^8$, or $COOR^9$; in which each of n and o, independently, is 0–4; $R^1$ is $C_{1-4}$ alkyl or $C_{1-4}$ acyl; each of $R^2$ and $R^3$, independently, is H, $C_{1-4}$ alkyl, or $C_{1-4}$ hydroxyalkyl; $R^4$ is H, $C_{1-4}$ alkyl, $C_{2-4}$ alkenyl $COR^2$, $COOR^{10}$, $C_{1-4}$ hydroxyalkyl or its acid ester or 2-tetrahydropyranyl ether, $C_{1-4}$ dihydroxyalkyl or its acid ester or 2-tetrahydropyranyl ether, $C_{1-4}$ halogenated alkyl; $OR^1$, or $NHR^7$; each of $R^5$ and $R^6$, independently, is H, CHO, $COR^1$, COOH, $COOR^9$, CN, or halogen; $R^7$ is H, $C_{1-4}$ alkyl, 2 -thienyl, mono-substituted phenyl, or di-substituted phenyl; $R^8$ is $COOR^2$, CO.CHO, $C_{1-4}$ hydroxyalkyl or its acid ester or 2-tetrahydropyranyl ether; and $R^9$ is H, $C_{1-4}$ alkyl, phenyl, mono-substituted phenyl, di-substituted phenyl, or 2-thienyl.

2. The method of claim 1, wherein m is 2, A is H, and $C\equiv CR^4$.

3. The method of claim 2, wherein $R^4$ is $C_{2-4}$ alkenyl, $C_{1-4}$ hydroxyalkyl or its acid ester or 2-tetrahydropyranyl ether, $C_{1-4}$ dihydroxyalkyl or its acid ester or 2-tetrahydropyranyl ether, or $C_{1-4}$ halogenated alkyl.

4. The method of claim 3, wherein $R^4$ is $C_{2-4}$ alkenyl.

5. The method of claim 3, wherein $R^4$ is $C_{1-4}$ hydroxyalkyl or tetrahydropyranyl ether.

6. The method of claim 5, wherein $R^4$ is $C_{1-4}$ hydroxyalkyl.

7. The method of claim 3, wherein $R^4$ is $C_{1-4}$ dihydroxyalkyl or tetrahydropyranyl ether.

8. The method of claim 3, wherein $R^4$ is $C_{1-4}$ halogenated alkyl.

9. The method of claim 3, wherein said compound is

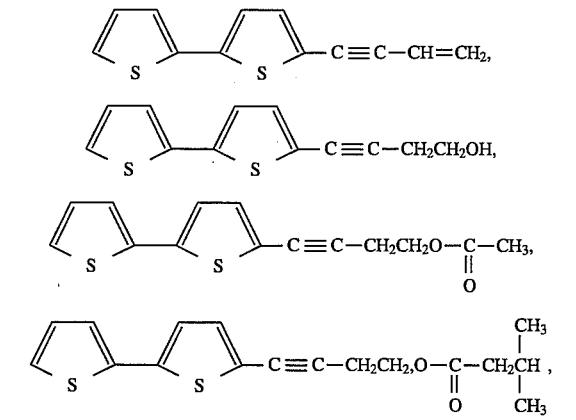

-continued

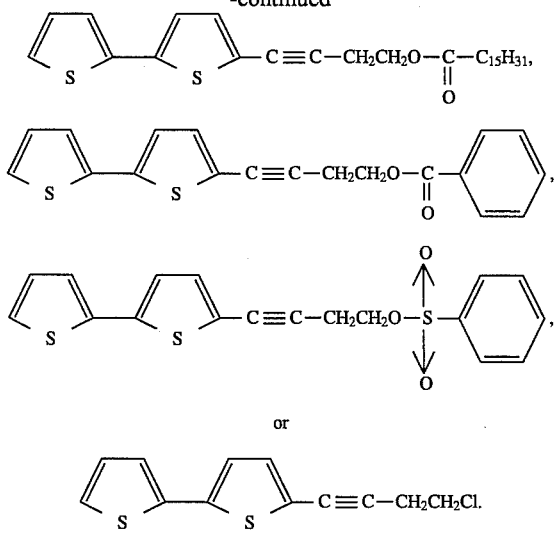

or

10. The method of claim 1, wherein m is 2–3, A is H or CO.CH$_3$, and B is CO.CH$_3$.

11. The method of claim 10, wherein m is 2–3, A is H, and B is CO.CH$_3$.

12. The method of claim 11, wherein m is 2.

13. The method of claim 10, wherein m is 2–3, A is CO.CH$_3$, and B is CO.CH$_3$.

14. The method of claim 13, wherein m is 2.

15. The method of claim 1, wherein m is 2–3; each of A and B, independently, is H, C$_{1-7}$ alkyl, (CH$_2$)$_n$CHO, (CH$_2$)$_o$COOH, C$_{1-7}$ hydroxyalkyl, NO$_2$, halogen, or CO.R$^1$.

16. The method of claim 1, wherein m is 2–3; A is H, C$_{1-7}$ alkyl, (CH$_2$)$_n$CHO, (CH$_2$)$_o$COOH, C$_{1-7}$ hydroxyalkyl, NO$_2$, halogen, or CO.R$^1$; and B is C$_{1-7}$ alkyl, (CH$_2$)$_n$CHO, (CH$_2$)$_o$COOH, C$_{1-7}$ hydroxyalkyl, NO$_2$, halogen, or CO.R$^1$.

17. The method of claim 15, wherein m is 2.

18. The method of claim 16, wherein m is 2.

19. The method of claim 15, wherein said compound is

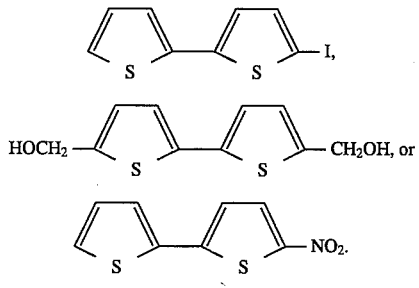

* * * * *